US006572638B1

(12) United States Patent
Dae et al.

(10) Patent No.: US 6,572,638 B1
(45) Date of Patent: *Jun. 3, 2003

(54) METHOD OF CONTROLLING BODY TEMPERATURE WHILE INHIBITING THERMOREGULATORY RESPONSES

(75) Inventors: Michael W. Dae, Belmont, CA (US); Timothy R. Machold, Moss Beach, CA (US); Wade A. Keller, San Jose, CA (US)

(73) Assignee: Radiant Medical, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/844,636

(22) Filed: Apr. 27, 2001

Related U.S. Application Data

(63) Continuation-in-part of application No. 09/372,714, filed on Aug. 11, 1999, now Pat. No. 6,231,594.

(51) Int. Cl.[7] .................................................. A61F 7/00
(52) U.S. Cl. ........................ 607/96; 607/106; 607/113
(58) Field of Search .......................... 607/96, 104, 105, 607/108–111, 113; 514/224.8, 282, 408–409, 225.5, 225.8

(56) References Cited

U.S. PATENT DOCUMENTS

| 4,544,664 A | 10/1985 | Karjalainen |
| 4,758,561 A | 7/1988 | Le Baut et al. |
| 4,758,562 A | 7/1988 | Adler et al. |
| 5,120,713 A | 6/1992 | Mugica |

(List continued on next page.)

FOREIGN PATENT DOCUMENTS

| WO | WO 98/26831 A1 | 6/1998 |
| WO | WO 98/31312 A1 | 7/1998 |
| WO | WO 01/10365 A1 | 2/2001 |

OTHER PUBLICATIONS

Chai, C. Y., et al., "Hypothermic Action of Chlorpromazine in Monkeys," Br. J. Pharmac., 1976, pp. 43–49, vol. 57.

(List continued on next page.)

Primary Examiner—Roy D. Gibson
(74) Attorney, Agent, or Firm—Robert D. Buyan; Stout, Uxa, Buyan & Mullins, LLP

(57) ABSTRACT

A method and apparatus for controlling the body temperature of a patient while reducing shivering by using a heat exchange device in combination with an anti-thermoregulatory response mechanism that temporarily reduces shivering. The devices disclosed include a catheter having a heat exchange balloon thereon with heat exchange fluid circulating through the interior of the balloon. The heat exchange balloon is placed in the vasculature of a patient, and heat exchange fluid at a temperature other than the temperature of the blood in the vasculature is circulated through the interior of the balloon to add or remove heat from the blood of the patient. Various anti-thermoregulatory response agents are disclosed including dopamine receptor blockers, dopamine receptor agonists, κ opioid receptor agonists, μ opioid receptor agonists opioid agonist-antagonist analgesics, serotonin 5 HT1a agonists, α2-adrenorceptor agonists, non-opiod analgesic monoamine uptake inhibitors and neuropeptides. Specific examples of each are give. A control system for the control of the patient's temperature is disclosed for controlling the patient's temperature in conjunction with administering the anti-thermoregulatory response mechanism.

105 Claims, 8 Drawing Sheets

U.S. PATENT DOCUMENTS

| | | | |
|---|---|---|---|
| 5,486,204 A | | 1/1996 | Clifton |
| 5,486,208 A | | 1/1996 | Ginsburg |
| 5,654,439 A | | 8/1997 | Pandey et al. |
| 5,863,934 A | | 1/1999 | Arnsten et al. |
| 6,149,673 A | | 11/2000 | Ginsburg |
| 6,156,057 A | | 12/2000 | Fox |
| 6,231,594 B1 | | 5/2001 | Dae |
| 6,299,599 B1 | | 10/2001 | Pham et al. |
| 6,410,554 B1 | * | 6/2002 | Broten et al. ............... 514/274 |
| 6,420,137 B1 | | 7/2002 | Strnad et al. |

OTHER PUBLICATIONS

Jessen, Claus, et al., "Intravascular Heat Exchanger for Conscious Goats," *Pflugers Archiv*, 1977, pp. 263–265, vol. 368.

Mercer, James B., et al., "Effects of Total Body Core Cooling on Heat Production of Conscious Goats," *Pflugers Archiv*, pp. 259–267, vol. 373.

Ripstein, Charles B., et al., "A Technique for the Production of Hypothermia," *Surgery*, 1953, pp. 98–103, vol. 35, No. 1.

* cited by examiner

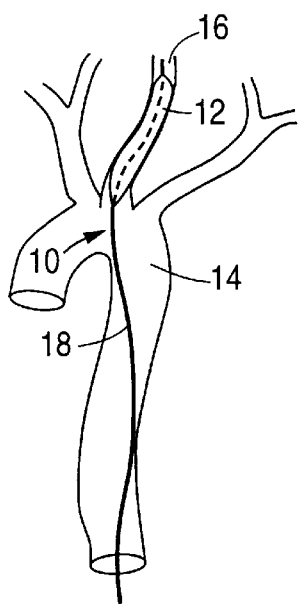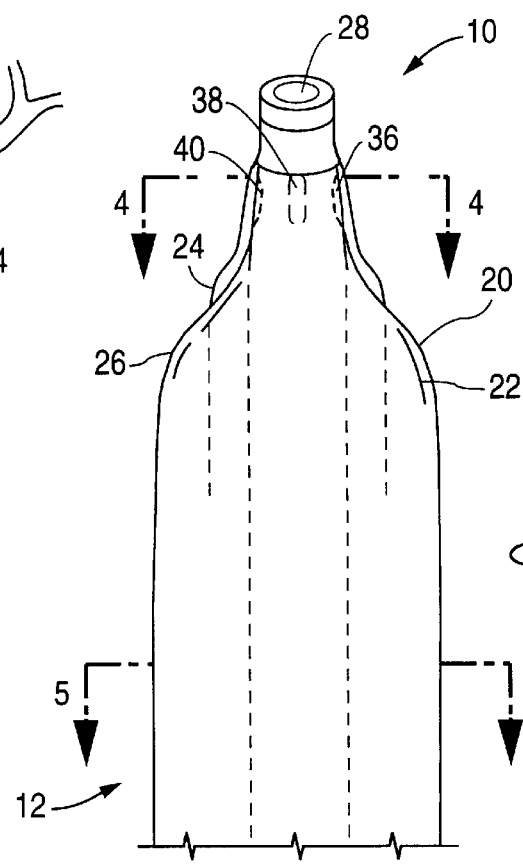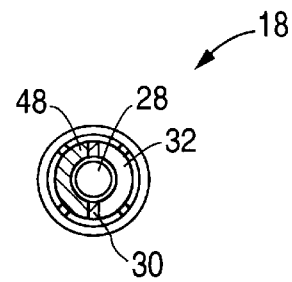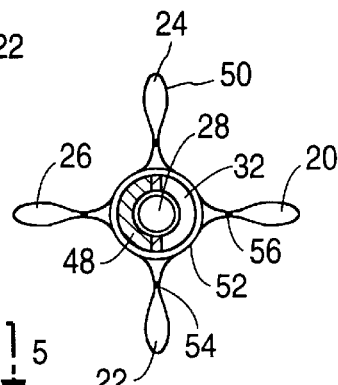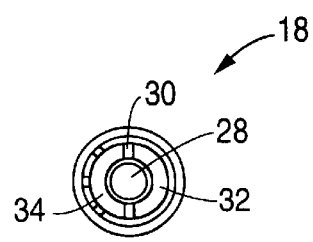
Fig. 2
Fig. 3
Fig. 4
Fig. 5
Fig. 6

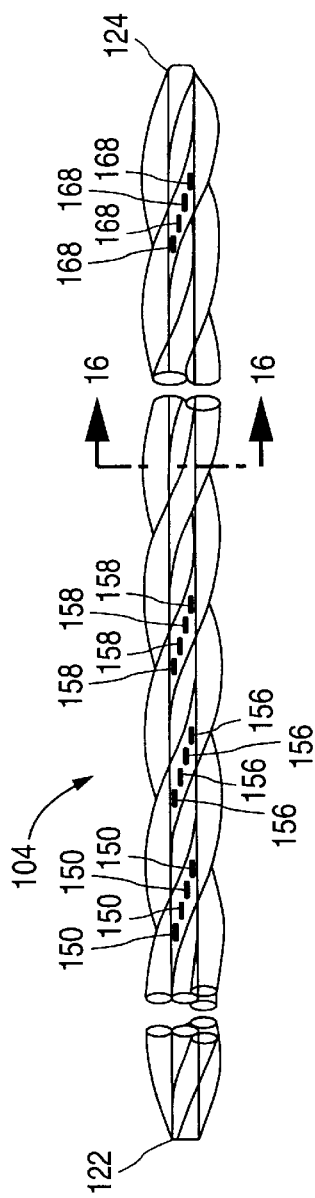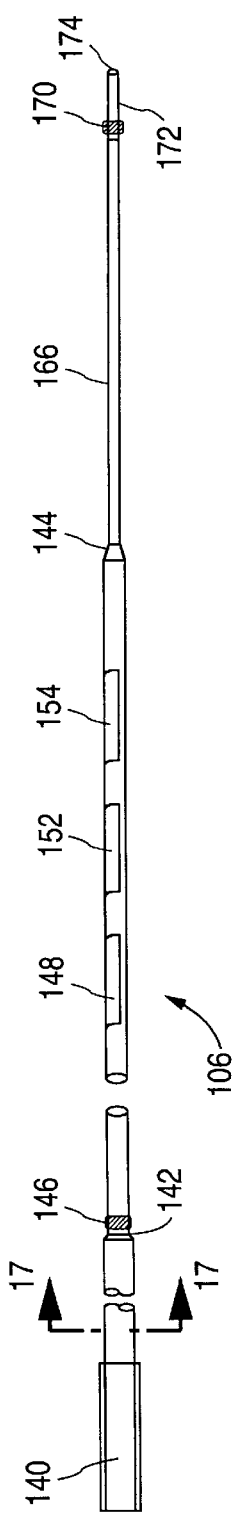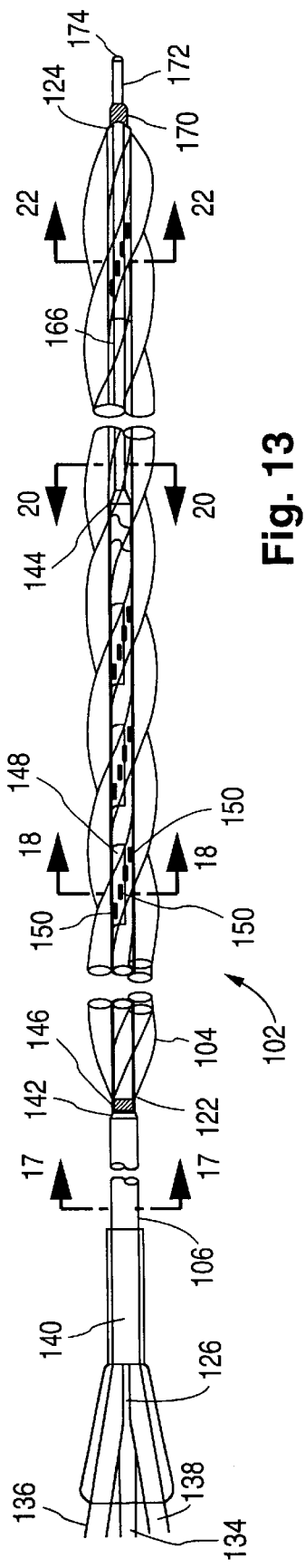

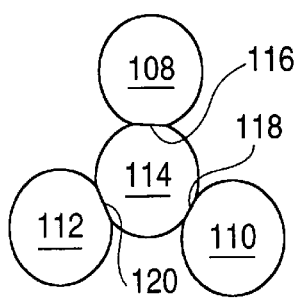
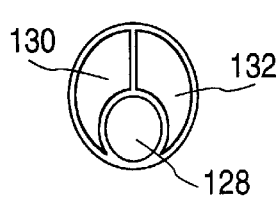
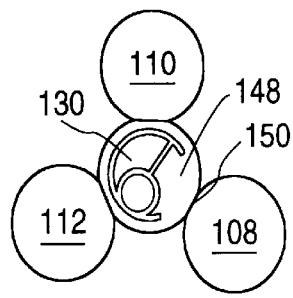
Fig. 16     Fig. 17     Fig. 18
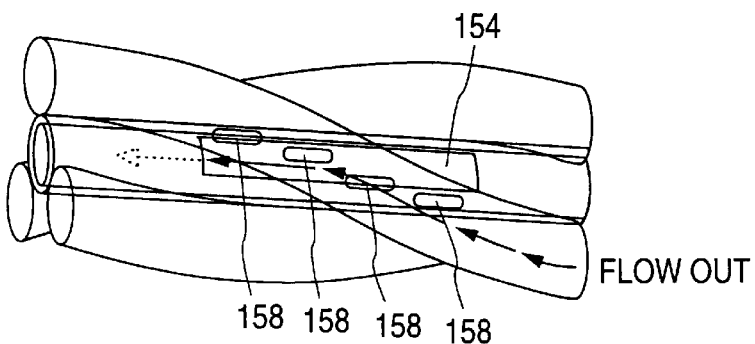
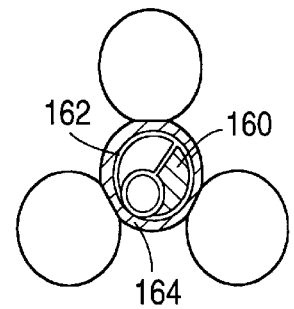
Fig. 19     Fig. 20
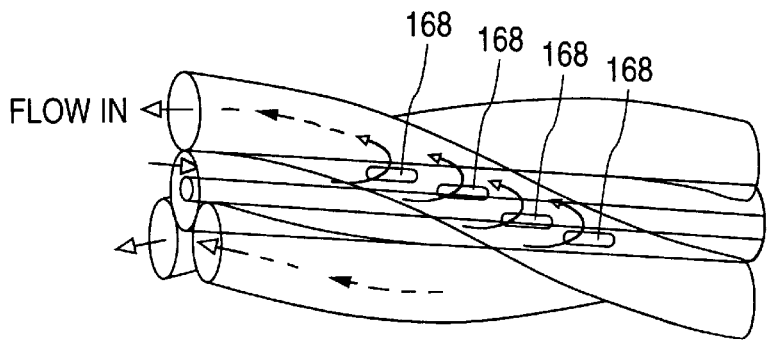
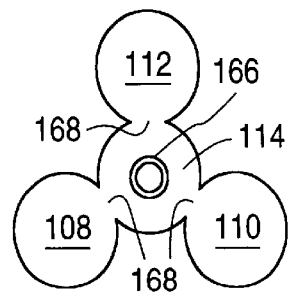
Fig. 21     Fig. 22

METHOD OF CONTROLLING BODY TEMPERATURE WHILE INHIBITING THERMOREGULATORY RESPONSES

CROSS-REFERENCE TO RELATED APPLICATIONS

This application is a continuation-in-part of U.S. Ser. No. 09/372,714, filed on August 11, 1999, now U.S. Pat. No. 6,231,594.

INTRODUCTION

1. Technical Field

This invention relates to a method, apparatus and composition for selectively controlling the temperature of all or a portion of a patient's body by lowering, maintaining or raising the temperature of a body fluid or tissue to affect the temperature of all or part of the patient's body, while reducing shivering that typically accompanies such temperature control. More particularly, the invention relates to the application of a method, apparatus and composition of a heat exchange device in combination with an anti-thermoregulatory response mechanism to control the temperature of all of a portion of a patient's body while reducing shivering, inhibiting vasoconstriction and/or increasing thermal comfort during various therapeutic uses of patient temperature control. The invention also relates to novel compositions that are useful for reducing shivering or inhibiting vasoconstriction.

2. Background

The "set point temperature" is the temperature that the body attempts to maintain through the thermoregulatory responses. Under ordinary circumstances, thermoregulatory responses within the human body which include sweating and vasodilation to enhance heat loss, arterio venous ("AV") shunting and vasoconstriction to enhance retaining heat, and shivering to enhance increased generation of body heat, serve to maintain the body at a near constant set point temperature of about 37° C. (98.6° F.), often referred to as "normothermic". However, sometimes the body sets a different set point temperature, for example a patient with a fever has an elevated set point temperature, and these mechanisms can serve to maintain an elevated temperature. In the case of a fever, the set point temperature can be higher than normothermic.

There is a temperature slightly below the set point temperature where the body senses that the body temperature is too low and begins to shiver. This temperature is sometimes referred to as the shivering threshold. As with the set point temperature, the shivering threshold is not an absolute temperature but varies between individuals and within the same individual depending on his or her condition.

As a result of the thermoregulatory responses, any heat lost to the environment is precisely balanced by heat produced within the body. Accordingly, attempts to control the body temperature below the set point temperature often produce shivering in the patient, as this is the main method of generating additional metabolic heat. Shivering can increase heat production by 200–500% and thus presents a serious obstacle when attempts are made to reduce a patient's body temperature. Even where the attempt is only to control the temperature at some constant temperature, if the patient is shivering this creates such a considerable amount of metabolic heat, and at such wildly varying rates, that precise control of the patient's temperature is often impossible.

The thermoregulatory responses provide a formidable defense when attempts are made to lower the body temperature below the set point temperature, for example, when one attempts to induce an artificially low body temperature (a condition known as hypothermia) by lowering the normothermic 37° C. to a lower temperature state or when one attempts to maintain normothermia by lowering an elevated body temperature to normothermic 37° C. Since there are numerous therapeutic reasons for both inducing hypothermia or inducing normothermia in a patient suffering from an elevated temperature, the thermoregulatory responses must be taken into consideration when designing a therapeutic regimen for controlling the temperature of all or a portion of a patient's body. Indeed, when the patient has a set point temperature that is above normothermic, for example when the patient has a fever, the shivering threshold may actually be above normothermic as well, and thus even an attempt to maintain a patient's temperature to normothermia may result in shivering. In addition, even when the thermoregulatory responses have been overcome, the body temperature may continue to drop, possibly below the desired threshold. This "overshooting" phenomenon can lead to complications. Accordingly, any therapeutic regimen for controlling body temperature preferably does so at a carefully monitored and controlled rate.

It has also been found that in rewarming a patient, either after therapeutic hypothermia or a patient suffering from accidental hypothermia, a very gradual and controlled rewarming rate is desirable. The dramatic generation of metabolic heat due to shivering, particularly in addition to heat added by other means, can result in rapid and uncontrolled rewarming. Therefore therapeutic rewarming at a carefully monitored and controlled rate also requires control over shivering.

Hypothermia may be induced to minimize damage to the brain when a patient has suffered a head injury or stroke, or to minimize damage to heart and brain tissue when a patient has undergone cardiac arrest. It may sometimes also be desirable to induce hypothermia during surgery, especially neurosurgery, once again to minimize tissue damage.

Early techniques involved application of cold to the skin surface or cooling the inspired air, alone or in combination with a compound to inhibit the thermoregulatory center such as chlorpromazine (Ripstein, et al., *Surgery* (35)1:98–103 (1954)). More recently, in situ blood temperature modification using a heat exchange catheter was described in Ginsburg, U.S. Pat. No. 5,486,208 and Ginsburg, WO 98/26831, the disclosures of which are incorporated herein by reference. This in situ procedure lowers the body temperature much faster and maintains the temperature at that lower level more precisely than the cooled skin surface or cooled breathing air methods described above.

There are also drugs which are capable of assisting in lowering body temperature. However, many require toxic doses in order to achieve the desired hypothermic state. Temperature lowering was also allegedly achieved with chlorpromazine, when administered in combination with a refrigeration blanket (Ripstein, et al, supra), and when administered alone (Chai, et al., *Br. J. Pharmac.* 57:43–49 (1976)). However, in both these instances, temperature variation after the chlorpromazine was administered was achieved by external cooling or exposure alone and without any significant control of the degree or rate of body cooling. More recently, hypothermia was allegedly induced in rats with a combination of a κ opioid receptor agonist and a dopamine receptor blocker or agonist (Adler, et al., U.S. Pat. No. 4,758,562).

It has been shown that the $\alpha_2$-adrenoreceptor agonists dexmedetomidine and clonidine are able to lower the shivering threshold (Talke, et al., *Anesthesiology* 87(4):835–841, 1997). In this study, patients at a normal temperature were warmed until sweating then cooled until shivering occurred, as the $\alpha_2$-adrenoreceptor agonist was administered. Evaluation of the ability of these agonists and a novel agonist to reduce core temperature were later described in Millan, et al., *The Journal of Pharmacology and Experimental Therapeutics* 295(3):1192–1205, 2000. However, in both these studies, as with chlorpromazine, temperature variation after the $\alpha_2$-adrenoreceptor agonist was administered was achieved with only minor control of the degree or rate of body cooling.

However, in spite of these advances, there continues to be a need to develop a method of safely and temporarily achieving thermoregulatory inhibition such as by inactivating the shivering response or inhibiting vasoconstriction while inducing hypothermia or otherwise reducing the body's temperature below its set point temperature for an extended period of time, or while gently and slowly raising the body's temperature from a hypothermic state. A number of therapeutic applications of hypothermia will greatly benefit from an ability to control shivering in an awake patient. The control of shivering and/or vasoconstriction is necessary whenever it is desirable to control the temperature of a patient that is not under general anesthesia (paralyzed and intubated) at a temperature that is below the shivering threshold. For example, in applying hypothermia or therapeutic cooling in at least the following situations, it would be beneficial to be able to control the patient temperature without causing the patient to shiver: treatment of myocardial infarct ("MI"); treatment of stroke; treatment of patients undergoing elective Percutaneous Transluminal Coronary Angioplasty ("PTCA"), maintaining normothermia in stroke and head trauma; treatment of cardiogenic shock; warming patients post-operatively after they are no longer under general anesthesia but are still below the shivering threshold, subsequent to major surgery especially where the surgery is either very long or involves significant exposure, as where there is a open thorax or abdomen, or where there is a craniotomy; treatment after cardiac arrest; and control of temperature in general where the patient is at a temperature below the shivering threshold but is not under general anesthesia. This invention is directed to such needs.

SUMMARY

The present invention pertains to a method for controlling the temperature of all or a portion of a patient's body to a temperature below its set point temperature, while achieving thermoregulatory response inhibition, comprising the steps of: (a) sensing the temperature of all or a portion of the patient's body; (b) generating a signal based upon the sensed temperature; (c) controlling the temperature of all or a portion of the patient's body based upon the signal; and (d) administering a therapeutically effective amount of an anti-thermoregulatory response agent to the patient. The method can further comprise the application of warmth to the skin of the patient.

The present invention also pertains to a method for providing therapeutic temperature control of all or a portion of a patient's body to a temperature below its set point temperature while reducing shivering in a patient that is being treated for a medical condition, comprising the steps of: (a) sensing the temperature of all or a portion of the patient's body; (b) generating a signal based upon the sensed temperature; (c) controlling the temperature of all or a portion of the patient's body based upon said signal by placing a heat exchange device having a heat exchange region into heat exchange proximity with the patient's body and controlling the temperature of the heat exchange region to control the temperature of all or a portion of the patient's body; (d) administering an anti-thermoregulatory response mechanism to the patient; and (e) maintaining the temperature of all or a portion of the patient's body at a therapeutically low temperature for a sufficient time to treat the medical condition.

The therapeutic temperature control may be directed to treatment of various medical conditions including myocardial infarct; of stroke; treatment of patients undergoing elective PTCA, maintaining normothermia in stroke and head trauma; treatment of cardiogenic shock; cardiac arrest; and control of temperature in general where the patient is at a temperature below the shivering threshold but is not under general anesthesia. The therapeutic temperature control may be also be directed to warming patients post-operatively after they are no longer under general anesthesia but are still below the shivering threshold, subsequent to major surgery especially where the surgery is either very long or involves significant exposure, as where there is a open thorax or abdomen, or where there is a craniotomy.

One object of this invention is to utilize the aforementioned method to lower a patient's body temperature below its set point temperature while reducing shivering.

Yet another object of this invention is to utilize the aforementioned method to raise a patient's body temperature from an initial temperature below the set point temperature while reducing shivering.

Another object of this invention is to utilize the aforementioned method to raise a patient's body temperature at a predetermined rate while reducing shivering.

Still another object of this invention is to utilize the aforementioned method to slowly and controllably rewarm a hypothermic patient from a temperature below the set point temperature toward normothermia.

Another object of this invention is to utilize the aforementioned method to maintain a patient's body temperature at a stable temperature below the set point temperature while reducing shivering.

Another aspect of the invention comprises controlling a patient's body temperature by placing a heat exchange device having a heat exchange region into the vascular system of the patient and controlling the temperature of the heat exchange region for a sufficient time to affect the temperature of all or a portion of the patient's body, while administering an anti-thermoregulatory response mechanism to the patient.

Still another aspect of the invention is a method of controlling a patient's body temperature by administering an anti-thermoregulatory response mechanism to the patient while using a heat exchange device that is a catheter and the heat exchange region comprises a balloon on the catheter, the temperature of the balloon being controlled by the circulation of a heat exchange fluid through the interior of the balloon. The catheter may have a shaft for the circulation of heat exchange fluid, where fluid circulates through the shaft and through the interior of the balloon.

It is another object of the invention to control the temperature of all or a portion of a patient's body by using a heat exchange device in combination with one or more anti-thermoregulatory response agents selected from the group consisting of: dopamine receptor blockers; dopamine receptor agonists; κ opioid receptor agonists; μ opioid receptor agonists; opioid agonist-antagonist analgesics; serotonin 5HT1a receptor agonists; α2-adrenoreceptor agonists; non-opiod analgesic monoamine uptake inhibitors; and neuropeptides.

Yet another aspect of the invention is a method of controlling the temperature of a patient by using a heat exchange device and administering an anti-thermoregulatory response agent selected from the group consisting of buspirone, ipsapirone, 8-hydroxy-2-(di-n-propylamino)tetralin, flesinoxan, dexmedetomidine, nepofam and neurotensin.

The present invention further comprises a method of controlling a patient's body temperature below its set point temperature with an internal heat exchange device, while simultaneously inactivating the shivering response of the patient.

One aspect of the invention pertains to a method of controlling the temperature of a patient below the set point temperature comprising the steps of: (a) employing internal in vivo core temperature regulation; and (b) administration of an anti-thermoregulatory response mechanism.

In another aspect of the invention, the step of employing internal in vivo core temperature regulation comprises placing a heat exchange device in the blood vessels of the patient, where the heat exchange device has a heat exchange region which is in contact with the flowing blood of the patient; and controlling the temperature of the heat exchange region for a sufficient time to affect the temperature of the patient, while administering an anti-thermoregulatory response mechanism to the patient.

Yet another aspect of the invention is a kit for controlling the temperature of a patient comprising a heat exchange device and an anti-thermoregulatory response mechanism. The kit may further comprising a set of instructions for use of the heat exchange device and/or administration of the anti-thermoregulatory response mechanism. The kit may also comprise a control system which measures patient body temperature and controls the heat exchange device in response to the body temperature.

Yet another aspect of the invention is to control the temperature of a patient while reducing shivering to treat a medical condition.

Yet another aspect of the invention is to control the temperature of a patient while reducing shivering to treat any condition where a metabolically active organ or portion of the patient's body is ischemic with temperature below the shivering threshold, including at least: myocardial infarct; stroke; to elective PTCA; to maintain normothermia in stroke and head trauma; to warm patients post-operatively after any major surgery especially where the surgery is either very long or involves significant patient heat loss, as where there is a open thorax or abdomen or a craniotomy; cardiogenic shock; cardiac arrest; or any condition while the patient is awake where it is desirable to control the patient temperature at some temperature below the shivering threshold.

These and other objects of the invention are achieved by the method, apparatus, kit and composition described herein where a patient's body temperature is lowered, such as by inducing hypothermia, utilizing a heat exchange device in combination with an anti-thermoregulatory response mechanism. Such device can comprise an elongate flexible catheter having a heat exchanger that operates to exchange heat between tissue, blood or other body fluid which flows in or is positioned in heat exchanging proximity thereto.

Further aspects and details of the present invention will become apparent to those of skill in the relevant art upon reading and understanding of the detailed description of preferred embodiments set forth here below. Each of the embodiments disclosed below may be considered individually or in combination with any of the other variations and aspects of the invention.

BRIEF DESCRIPTION OF THE DRAWING

FIG. 2 illustrates a heat exchange device having a heat exchange region positioned within the left common carotid artery.

FIG. 3 depicts a heat exchange catheter having a heat exchange balloon and a plurality of heat transfer fins.

FIG. 4 is a cross-sectional view of the distal end of the catheter taken along line 4—4 of FIG. 3.

FIG. 5 is a cross-sectional view of the central section of the catheter taken along line 5—5 of FIG. 3.

FIG. 6 is a cross-sectional view of the proximal end of the catheter taken along line 6—6 of FIG. 3.

FIG. 13 depicts another embodiment a heat exchange catheter, as assembled.

FIG. 14 shows the shaft member of the catheter assembly of FIG. 13.

FIG. 15 illustrates the balloon configuration of the catheter assembly of FIG. 13.

FIG. 16 is a cross-sectional view of the balloon of FIG. 15 taken along line 16—16.

FIG. 17 is a cross-sectional view of the shaft of FIG. 13 taken along line 17—17.

FIG. 18 is a cross-sectional view of the catheter of FIG. 13 taken along line 18—18.

FIG. 19 is a view of a portion of the catheter of FIG. 13 illustrating outflow of heat exchange fluid.

FIG. 20 is a cross-sectional view of the catheter of FIG. 13 taken along line 20—20.

FIG. 21 is a view of a portion of the catheter of FIG. 13 illustrating inflow of heat exchange fluid.

FIG. 22 is a cross-sectional view of the catheter of FIG. 13 taken along line 22—22.

DETAILED DESCRIPTION

Figure 1:
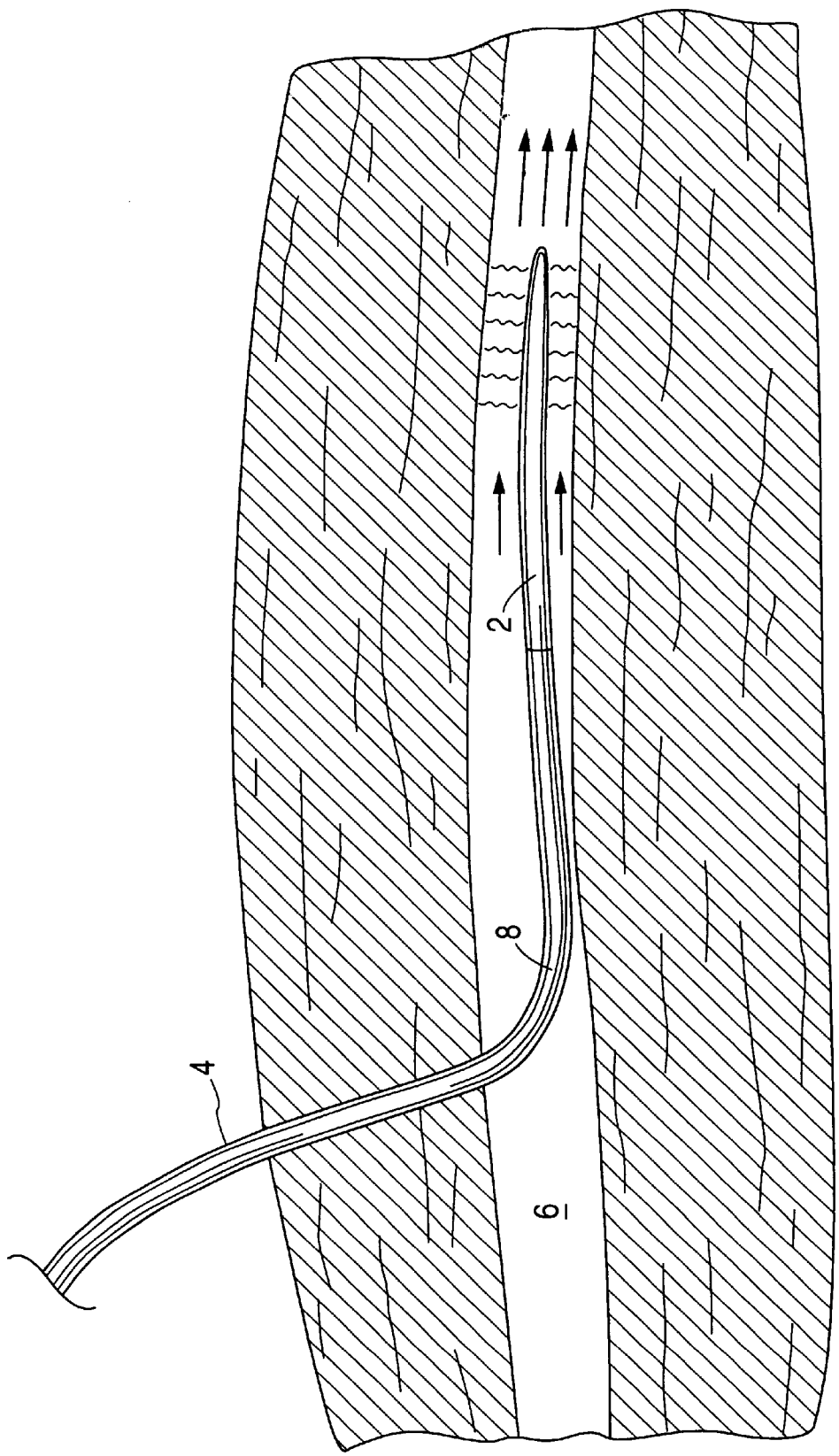
FIG. 1 depicts a heat exchange device inserted percutaneously into a blood vessel of a patient.

The present invention comprises a method of controlling a patient's body temperature to a temperature below its set point temperature, such as inducing hypothermia, while simultaneously combating thermoregulatory responses of the patient. More specifically, the invention provides for a method, apparatus, kit and composition for reducing the body's temperature below its set point temperature for an extended period of time while temporarily inactivating the shivering response.

Inactivation of the thermoregulatory responses allows one to lower the body temperature below the set point temperature while reducing shivering and/or inhibiting vasoconstriction in the patient. The methods described herein inactivate the thermoregulatory responses by means of an anti-thermoregulatory response mechanism that can be administered prior to, simultaneous with, or subsequent to initiation of the temperature controlling step, for example the temperature lowering step.

Before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. Additionally, when examples are given, they are intended to be exemplary only and not to be restrictive. For example, when an example is said to "include" a specific feature, that is intended to imply that it may have that feature but not that such examples are limited to those that include that feature.

The term "set point temperature" is used herein to refer to the temperature that the body attempts to maintain through the thermoregulatory responses. The set point temperature can vary both between individuals and within the same individual at different times. For example, in a healthy individual, the set point temperature is usually about 37° C. However, the set point temperature can be changed, for example when an individual is ill and the body develops a fever. In that instance the thermoregulatory responses actually work to maintain a higher than normal body temperature. Thus, in such circumstances the set point temperature can be higher than 37° C.

As used herein, the term "lowered temperature state" is intended to mean a state where the temperature of all or a portion of a patient's body has been reduced to a temperature below the set point temperature. The term "lowered temperature state" includes, for example, the lowering of an elevated body temperature to normothermic (about 37° C.). Here, the set point temperature is a fever and the body temperature is reduced to 37° C., a temperature below the fevered set point temperature. More typically, the term "reduced temperature state" refers to a "hypothermic state", which can occur when the normal body temperature of 37° C. is reduced to a lower temperature, i.e., the set point temperature is a normal 37° C. state and the body temperature is reduced to below 37° C. Typically, hypothermia may be induced by lowering the patient's temperature until it is about 32° C. It is understood, however, that these temperature values provide a useful basis for discussion but definitions vary widely in the medical literature.

As used herein the term "normothermic" is intended to mean a temperature of about 37° C. (98.6° F.).

As used herein, the term "shivering" is intended to mean the uncontrolled muscle movement that an animal typically experiences when cold that does not result in controlled and coordinated movement of the organism, and includes, for example, trembling and quaking. More precisely, the term is used to mean the, trembling or quaking that an animal experiences when it's body temperature falls to a certain temperature below its set point temperature, said "certain temperature" sometimes being referred to as the "shivering threshold".

As used herein, the term "reduce" as it pertains to shivering is intended to include minimizing shivering to a noticeable degree, eliminating shivering in its entirety or preventing shivering from starting.

As used herein, the term "patient" will typically be mammalian, and most commonly a human. As such, the term "therapeutically effective amount" is intended to mean a dosage sufficient to reduce shivering in the patient being treated, and will vary depending upon various factors such as the patient species, the particular anti-thermoregulatory response agent(s) used, the patient's age, weight and other characteristics, including any individual sensitivity.

In general, the method of the invention relates to controlling the temperature of all or a portion of a patient's body to a temperature below its set point temperature, while reducing shivering. One example of the method of the invention comprises the steps of: (a) sensing the temperature of all or a portion of the patient's body; (b) generating a signal based upon the sensed temperature; (c) controlling the temperature of all or a portion of the patient's body based upon the signal; and (d) administering an anti-thermoregulatory response mechanism to the patient. This latter step can involve administering a therapeutically effective amount of one or more anti-thermoregulatory response agents to the patient, applying warmth to the skin of a patient, or both administering the agent(s) and applying warmth.

As used herein, the term "controlling the temperature" is intended to include lowering the temperature below the set point temperature, raising the temperature from an initial temperature below the set point temperature, raising the temperature at a predetermined rate or increase, and maintaining the temperature at a stable temperature below the set point temperature. Such stable temperature can be, for example, normothermia.

An example of one such method comprises the steps of: (a) positioning a heat exchange device within the patient and in heat exchanging proximity to body fluid such as blood; (b) utilizing the device to lower the temperature of said body fluid to a sufficient degree and for a sufficient duration to alter the temperature of said body; and (c) administering an anti-thermoregulatory response mechanism to the patient. As used herein, the term "utilize" is intended to include, for example, activating the device, adjusting the thermal output of the device and deactivating the device. The positioning step can involve, for example, placing a heat exchange device having a heat exchange region into the vascular system of the patient. The temperature of the heat exchange region is then controlled for a sufficient time to affect the temperature of the patient.

Although the methods of the invention may be used to cool the entire patient's body, they may be useful in cooling a specified portion of a patient's body. For example, the methods of the invention may cool the brain or a portion thereof to deter neural damage following a stroke or other insult (e.g., period of ischemia, period of hypoxia, hemorrhage, trauma, etc.). In this manner, the heat exchange device would be positioned in a blood vessel which leads to the brain, such as the right common carotid artery, left common carotid artery, innominate artery, right internal carotid artery, left internal carotid artery, and so forth. Alternatively, the heat exchange device may be positioned in a large vein such as the inferior vena cava and heat removed from the blood for a sufficient length of time to cool the entire body and thus cool the neural tissue, such as the brain and spinal cord, as well.

It may also be desirable to cool the entire patient's body such as a febrile patient. For example, in stroke patients who have become febrile, it may be therapeutically desirable to reduce the body's temperature to normothermia. In particular, the methods of the invention find utility in treating patients that have suffered a stroke, since stoke patients often develop a fever. Even a slight fever in these cases is correlated with much worse outcomes than in patients who do not have a fever. In such cases, it is advantageous to maintain the patient at normothermia. However, since patient's with a fever often have their set point reset to a temperature above normothermia, even reducing the patient's temperature to normal in those cases may trigger shivering with the attendant problems.

The methods of the invention are useful in minimizing tissue damage and other adverse affects of a variety of illnesses. In addition, these methods can be used in combination with existing therapies that are being administered to treat illness.

The methods of the invention find particular utility in the treatment of patients that have suffered a myocardial infarction or cardiac arrest. These methods are also useful to treat patients that are suffering from cardiogenic shock and in conjunction with the elective PTCA.

For those patients suffering from these and similar conditions, the methods of the invention are useful to control the temperature of all or a portion of a patient's body to a temperature below its shivering point temperature. For example, the method can serve to cool a specified portion of or the entire patient's body, such as cooling the brain or a portion thereof to deter tissue damage following such illness or elective surgery. In an exemplary method of the invention, the heat exchange device can be positioned in a blood vessel which leads to the brain, such as the right common carotid artery, left common carotid artery, innominate artery, right internal carotid artery, left internal carotid artery, and so forth. Alternatively, the heat exchange device can be positioned in a large vein such as the inferior vena cava and heat is removed from the blood for a sufficient length of time to cool the entire body and thus cool the neural tissue, such as the brain and spinal cord, as well.

The methods of the invention serve to lower the temperature to a temperature below its set point temperature or elevate the temperature from a temperature below its set point temperature, or to control the temperature at some temperature while simultaneously inactivating the thermoregulatory response by means of an anti-thermoregulatory response mechanism. The order of the steps of the method can be conducted several ways in that the anti-thermoregulatory response mechanism can be administered prior to, simultaneous with, or subsequent to initiation of the temperature lowering or raising step. In this manner, the anti-thermoregulatory response mechanism can be administered to the patient: prior to controlling the body temperature, for example, prior to positioning a heat exchange device; after positioning the device but before utilization; simultaneous with the utilization step (b); or subsequent to the utilization step.

Figure 23:
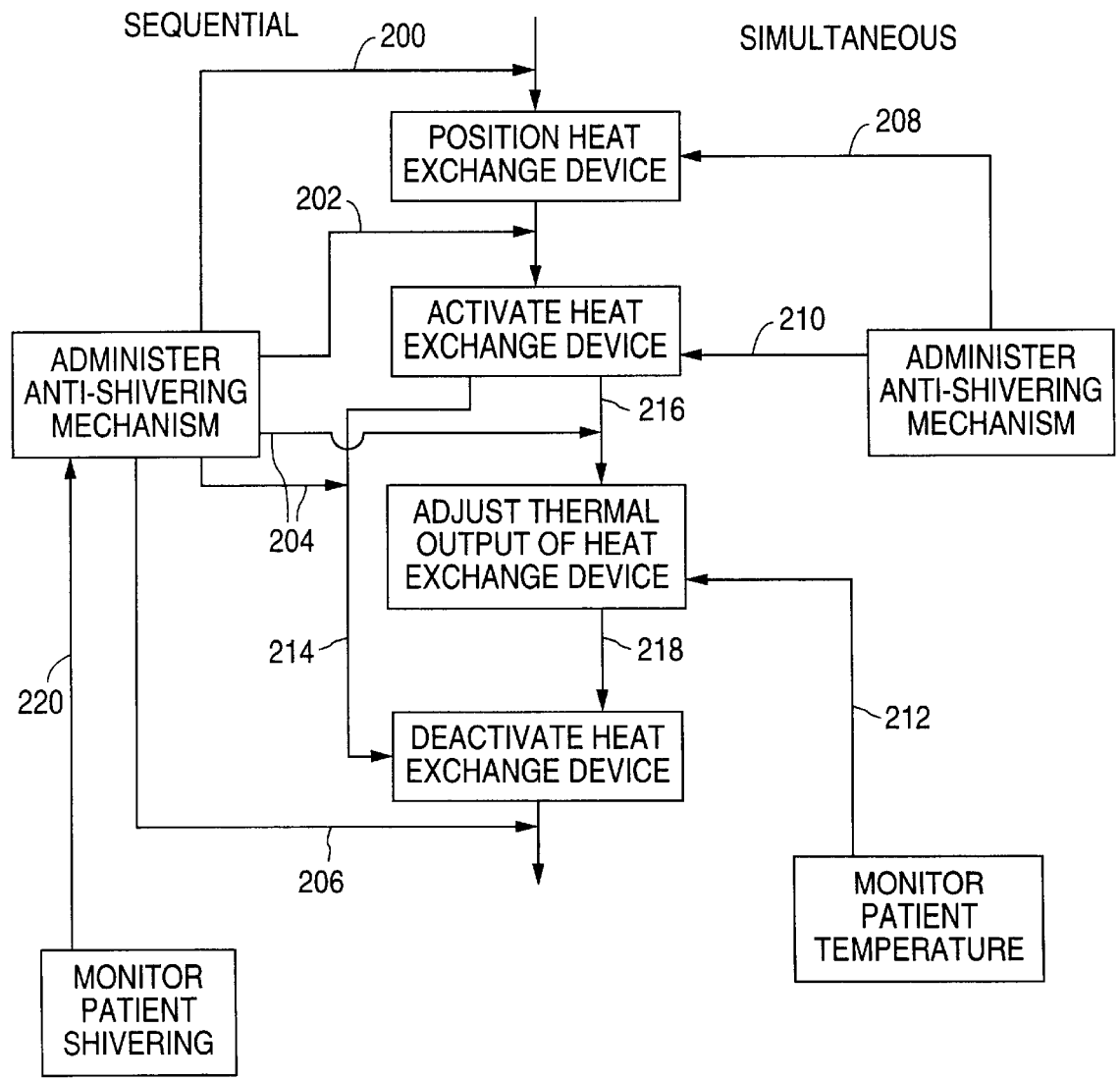
FIG. 23 is a flow chart illustrating a preferred method of the invention.

Several acceptable methods are illustrated in FIG. 23 in the form of a flow chart. For sequential administration routes, the anti-thermoregulatory response mechanism can be administered before positioning the heat exchange device (200), after the device has been positioned (202), after the device has been activated (204), or after the device has been deactivated (206), the latter being useful if it is desired to administer the anti-thermoregulatory response mechanism after the body has already been cooled to the desired temperature. For simultaneous administration routes, the anti-thermoregulatory response mechanism can be administered simultaneously with the positioning of the heat exchange device (208) or while the device is activated (210). The invention also contemplates administering the anti-thermoregulatory response mechanism in any combination of the aforementioned sequential and simultaneous routes.

In another aspect of the invention, a method of controlling the temperature of a patient below the set point temperature comprises the steps of: (a) employing internal in vivo core temperature regulation; and (b) administration of an anti-thermoregulatory response mechanism. One means of employing internal in vivo core temperature regulation comprises placing a heat exchange device in the blood vessels of the patient, where the heat exchange device has a heat exchange region that is in contact with the flowing blood of the patient. The temperature of the heat exchange region can then be controlled for a sufficient time to affect the temperature of the patient. The heat exchange device may be a catheter having a shaft for the circulation of heat exchange fluid therein. The heat exchange region can be a balloon; and the temperature of the heat exchange region is controlled by circulation of heat exchange fluid through the shaft and the interior of said balloon.

As noted above, the cooling or warming aspect of the invention operates to cool or warm the entire patient's body to lower or raise the patient's body temperature, or to cool or warm a portion of the patient's body, for example, to minimize damage to a particular body tissue.

In a preferred method of the invention, the body temperature is controlled by cooling (or raised by warming) a body fluid in situ for a sufficient length of time to lower (or raise) the temperature by the desired amount, while reducing patient shivering that typically accompanies such cooling (or warming) by administering an anti-thermoregulatory response mechanism. Typical body fluids include, blood, cerebral spinal fluid, peritoneal fluid or the like, but will typically be blood. In addition, the methods of the invention will generally result in in situ cooling or warming of target body tissues and organs, either by cooling or warming body fluid directed to the tissue, for example, as in cooling the brain by cooling blood flowing through the carotid artery, or by cooling the whole body which results in cooling the target tissue. Typical body tissues and organs that may be the target tissue include, neural tissue, brain, heart, spinal cord tissue, kidney, liver and the like, but will typically be the heart and the brain.

The heat exchange device itself may have a temperature within the range of 0 to 42° C. By controlling the temperature of the portion of the device that is in heat exchanging proximity to the body fluid so that a temperature differential ($\Delta T$) exists between the heat exchange device and the body fluid, heat is transferred between the device and the body fluid. For example, when the body temperature is lowered by cooling blood, the heat exchange device is positioned within a blood vessel and maintained with a temperature below that of the blood flowing past the heat exchange device so that heat is transferred between the device and blood flowing through the vessel. Blood flows in heat transfer proximity to the heat exchange device and is cooled. By continuing to cool fluid flowing past the heat exchanger in sufficient volume and for a sufficient length of time, the temperature of the patient is reduced. The methods of the invention are suited to lower the body temperature of a patient by as much as 9° C. It is not expected to reduce the patient's body temperature to less than 28° C., and preferably not lower than 32° C.

Another important aspect of the instant invention is that the temperature of the patient's body or portion thereof can be reduced controllably, thus avoiding the problems associated with cooling a patient too rapidly, or below a desired temperature. Likewise, when a hypothermic patient is warmed, the combination of an internal heat exchange device controlled by feedback with anti-thermoregulatory response agents that reduce the body's shivering and/or inhibit vasoconstriction and thus allow more precise control over the patient's temperature, permits a more gradual and gentle warming of the patient. It will be readily seen that if a patient is maintained at a reduced temperature below the set point temperature and particularly below the shivering threshold, the administration of anti-thermoregulatory response agents in combination with feed-back controlled in vivo heat exchange permits a more effective temperature control of the patient. In particular, when inducing hypothermia, a target tissue can be cooled to the desired temperature and that temperature maintained by controlling the heat exchange device. This is shown schematically in FIG. 23, where feedback information is obtained from the patient, for example, the patient's temperature is measured (either the temperature of the entire body, the target tissue or fluid), and that feedback information is used in a feedback system (212) to continually control or adjust the output of the heat exchange device. In this manner, the feedback system may be used to achieve or maintain, for example a pre-determined body or body fluid temperature, a pre-determined heat exchange device temperature or a pre-determined ΔT. This is optional, however. The methods of the invention are well suited for use where the device may operate in a simple on-off mode. That is, it may operate at full power until deactivated (214) or where the device is activated, adjusted one or more times during its operation (216) and then deactivated (218). Feedback information can also be obtained from the patient regarding the amount of shivering being experienced and this feedback system (220) can be used to continually control or adjust the administration of the active agent.

Generally the methods of the invention will involve affecting the temperature of the entire body, but different regions may be controllably maintained at temperatures different from each other, for example, by controlling different heat exchange devices at different locations with the patient's body.

In one embodiment of the invention, the heat exchange device is positioned within the patient, preferably intravascularly. For example, the heat exchange device, such as a catheter, is inserted through a puncture or incision into a fluid containing portion of the patient's body, for example, percutaneously into a blood vessel. An internally positioned device, i.e., core cooling, is advantageous as it circumvents vasoconstriction. Accordingly, in one embodiment of the invention, a method of controlling a mammalian patient's temperature below the patient's set point temperature, while inhibiting the patient's thermoregulatory responses, comprises the steps of (a) positioning a heat exchange device in a blood vessel, for example a blood vessel leading to the vena cava or brain; (b) utilizing the device to decrease the temperature of blood which passes in heat exchanging proximity to the heat exchange device; and (c) administering an anti-thermoregulatory response mechanism to the patient.

The heat exchange device can have the configuration of a number of medical devices that are well known in the art. Although a catheter is preferred, it is understood that any other suitable means of cooling the body and/or target fluid or tissue is suitable for use in the instant invention, and that the particular catheter configurations described herein are intended to be exemplary and not limiting in any manner. The preferred heat exchange mechanism involves heat exchanger in contact with a body fluid or tissue on its external surface, the heat exchanger being chilled or heated on its internal surface by circulation of a chilled fluid which is preferably sterile saline or other biocompatible fluid having appropriate heat transfer characteristics.

In one embodiment of the invention, a method of controlling a patient's temperature comprises utilizing a heat exchange device which is a catheter. In addition, an anti-thermoregulatory response mechanism as defined below, is administered to the patient to reduce shivering and/or inhibit vasoconstriction. A suitable catheter comprises an elongate flexible catheter having a heat exchanger which is capable of exchanging heat between blood or other body fluid which flow in heat exchanging proximity thereto. For example, a catheter having a heat exchanger or heat exchange region which may be, for example, a balloon with fins, is inserted through a puncture or incision into a fluid containing portion of the patients body, for example, a blood vessel. The temperature of the balloon is controlled by the circulation of a heat exchange fluid through the interior of the balloon. Blood flows in heat transfer proximity past the heat exchanger. Heat exchange proximity requires sufficient proximity for effective heat exchange to occur and depends on such factors as the chemical and physical make-up of the blood, the rate of flow past the heat exchange surface, the pattern of blood flow past the heat exchanger, (laminar flow, turbulent flow, and the like), the difference in temperature between the heat exchange surface and the blood, the material of which the heat exchange surface is made, and the proximity between the heat exchange surface and the blood. By continuing to cool fluid flowing in heat transfer proximity for a sufficient length of time, the body temperature of the patient is altered.

Anti-thermoregulatory Response Mechanism

As used herein, the term "anti-thermoregulatory response mechanism" is intended to include the administration of one or more anti-thermoregulatory response agents to a patient, the application of warmth to the skin of a patient, or a combination thereof.

Warmth can be applied to the skin in numerous ways. Exemplary warming devices include, by way of illustration and not limitation, warming blankets, heating pads, or any other configuration or device suitable for covering the skin surface to be warmed; heat exchangers; devices that operate by administering thermal energy such as radiant heat lamps; and so forth. Warmth is preferably applied to the skin in such a manner and for such duration so as to maintain the skin temperature at about 36–39° C.

As used herein, the term "anti-thermoregulatory response agent" is intended to mean any biologically active agent or drug or combination of agents or drugs, that is administered to a patient for the purpose of reducing shivering, inhibiting vasoconstriction and/or increasing thermal comfort. The term is also intended to include pharmaceutically acceptable salts or variants of such agents which retain the biological effectiveness of the agents themselves. Such salts are often preferred as the salt form of the anti-thermoregulatory response agent may have better solubility, increased duration of action, and so forth. Suitable salts are well known to those of skill in the art and may include the hydrochloride, methanesulfonate, mesylate, maleate, decanoate, enanthate, succinate, lactate, sulfate, and quaternary ammonium salts.

The anti-thermoregulatory response agents suitable for use in the methods of the invention, include by way of illustration and not limitation, sedatives, hypnotics, antipsychotics, anxiolytics, opioids, and drugs that selectively affect specific neurotransmitter systems. In most cases, however, when administered alone, a high dosage may be required to achieve a desired temperature drop. In the instant invention, the reduced temperature state is induced by a heat exchange device, such as a cooling catheter, while the anti-thermoregulatory response agent is used to overcome shivering. Several agents from the same or different classes may also be administered in combination. In this manner, small non-toxic dosages can be administered to achieve the desired anti-thermoregulatory response results. Accordingly, the suitability of an anti-thermoregulatory response agent for use in the methods described herein depends upon its ability to suppress the thermoregulatory responses to reduce shivering and/or inhibit vasoconstriction during cooling and thereafter while the patient is maintained at a temperature that would otherwise produce shivering or vasoconstriction.

Preferred anti-thermoregulatory response agents include dopamine receptor blockers (neuroleptic drugs and dopamine receptor agonists), opioids including morphine, opioid receptor agonists and antagonists such as kappa (κ) opioid receptor agonists, mu (μ) opioid receptor agonists, opioid agonist-antagonist analgesic drugs, serotonin receptor agonists such as serotonin HT1a receptor agonists, $\alpha_2$-adrenoreceptor agonists such as dexmedetomidine, non-opiod analgesic monoamine uptake inhibitors such as nepofam and neuropeptides such as neurotensin, as well as pharmaceutically acceptable salts or variants of any of the aforementioned agents. Combinations of these anti-thermoregulatory response agents are also contemplated.

There are numerous dopamine receptor blockers (neuroleptic drugs and dopamine receptor antagonists), or mixtures thereof that are suited for use in the methods of the invention. Suitable dopamine receptor blockers include phenothiazines, in particular those having one or more aliphatic, piperidine and piperazine groups such as are described Adler, et al., U.S. Pat. No. 4,758,562, the disclosure of which is incorporated herein by reference. Exemplary phenothiazines include, by way of illustration and not limitation, aliphatic, halogenated phenothiazines such as chlorpromazine, triflupromazine, and the like; piperidine phenothiazines such as thioridazine, mesoridazine, piperacetazine, and the like; piperazine phenothiazines such as fluphenazine, trifluoperazine, acetophenazine, carphenazine, fluphenazine, perphenazine, prochlorperazine and the like. Phenothiazines can also be described by the following formula:

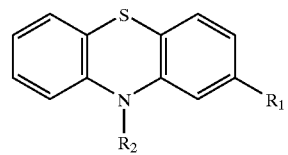

where:
$R_1$ is selected from the group consisting of —H; halo (Cl, F, Br or I atoms); haloalkyl (preferably having 1–20 carbon atoms and at least one fluorine, chlorine, bromine, iodine atom) such as trifluoromethane; alkyl such as methyl, propyl, t-butyl, hexyl, cyclopropyl, and so forth; alkoxy such as methoxy, propoxy, hexoxy, and so forth; and any other group that will not adversely affect the biological activity of the nucleus, i.e., that will not deactivate or hinder the nucleus to the extent that its effect becomes neutralized. As used herein, the term "alkyl" is intended to mean a monovalent radical containing only carbon and hydrogen atoms, and is a fully saturated branched or straight chain radical, a cycloaliphatic ring of carbon atoms linked together by single bonds, or a mixture of aliphatic groups. The alkyl group preferably comprises about 1–20 carbon atoms, with preferably a maximum of 5 carbons atoms in the chain. As used herein, the term "alkoxy" is intended to mean an alkyl radical attached to the remainder of a molecule by an oxygen atom. The alkoxy group preferably comprises about 1–20 carbon atoms.

$R_2$ is selected from the group consisting of halo (Cl, F, Br or I atoms), an aliphatic group having a terminal nitrogen atom, preferably a tertiary amino nitrogen atom (e.g., dimethylamino group), an aliphatic group having a terminal piperidine substituent, and an aliphatic group having a piperazine substituent, or any other substituent that will not adversely affect the biological activity of the nucleus. The aliphatic substituent can be straight chained (preferably having no more than 5 carbons atoms in the chain), branched (preferably having no more than 10 carbons atoms in the chain), cyclic, or mixed aliphatic, with any number of carbon atoms (preferably 1–20), and may optionally contain one or more hetero atoms (O, N, S and the like). The terminal nitrogen atom can be attached to a chain. Optionally, the nitrogen atoms can be contained in a cycloaliphatic ring structure such as piperidine, piperazine, substituted piperidine, substituted piperazone, and the like, where the cycloaliphatic ring can contain any of a number of suitable substituents having similar characteristics as described above for $R_1$. In those instances where $R_2$ contains a substituted or unsubstituted piperazine ring, the chain does not require a terminal nitrogen containing group. The piperazine ring may be located anywhere along the aliphatic chain.

A particularly preferred dopamine receptor blocker for use in the methods of the invention is the phenothiazine dimethylaminopropyl-N-chlorophenothiazine, commonly known as chlorpromazine and its hydrochloride salt, commonly known as thorazine.

Other suitable anti-thermoregulatory response agents for use in the methods of the invention include dopamine receptor blockers such as neuroleptic drugs, which include by way of illustration and not limitation, thioxanthenes such as chlorprothixene, thiothixene, and the like; diphenylbutylpiperidines such as pimozide, penfluridol, and the like; dibenzoxazepines such as loxapine, and the like; dibenzodiazepines such as clozapine, and the like; benzamides such as sulpiride, and the like; and butyrophenones such as haloperidol and the like; along with dopamine b-hydroxylase blockers such as disulfiram; and mixtures of any of the foregoing dopamine receptor blockers. Haloperidol is a particularly preferred neuroleptic drug.

Other suitable anti-thermoregulatory response agents for use in the methods of the invention include dopamine receptor agonists, which include by way of illustration and not limitation, amantadine, bromocriptine, piribidil, apomorphine, lisuride, pergolide, mesulergine, and so forth.

Suitable κ opioid receptor agonists include, by way of illustration and not limitation, bremazocine, nalorphine, ketazocine and alkyl ketazocines such as ethylketazocine, tifluadom, trans-3,4-dichloro-N-methyl-N-[2-(1-pyrrolidinyl)cyclohexyl]benzene acetamide, (5a,7a,8B)-N-methyl-N-[7-(1-pyrrolidinyl)-1-oxaspiro(4,5)-dec-8-yl] benzene acetamide, meperidine and the like, along with their pharmaceutically acceptable salts such as bremazocine hydrochloride, nalorphine hydrochloride, ketazocine salts including alkyl ketazocine methanesulfonates such as ethyl ketazocine methanesulfonate, trans-3,4-dichloro-N-methyl-N-[2-(1-pyrrolidinyl) cyclohexyl] benzene acetamide methanesulfonate, and the like and mixtures thereof. Such κ opioid receptor agonists are described in detail in Adler, et al., supra. Preferred κ opioid receptor agonists include trans-3,4-dichloro-N-methyl-N-[2-(1-pyrrolidinyl) cyclohexyl]benzene acetamide, its methanesulfonate salt, and (5a,7a,8B)-N-methyl-N-[7-(1-pyrrolidinyl)-1-oxaspiro (4,5)-dec-8-yl]benzene acetamide and meperidine.

Meperidine may also be characterized as a suitable μ opioid receptor agonist and indeed that may be its majority pharmacological activity.

Opioid agonist-antagonist analgesic drugs are compounds that act as partial agonists at opioid receptors. A "partial" agonist" is one that binds to the receptor but has low intrinsic activity so that its dose-response curve has a ceiling effect less than that produced by a full agonist. Such compounds are described in Hoskin, et al., *Drugs* 41(3):326–344 (1991), the disclosure of which is incorporated herein by reference. Suitable opioid agonist-antagonist analgesic drugs include, by way of illustration and not limitation, nalorphine and nalorphine-like agonist-antagonists such as pentazocine, buprenorphine, butorphanol, nalbuphine, cyclazozine, dezozine and nalorphone. Preferred opioid agonist-antagonist analgesic drugs include, pentazocine, butorphanol and nalbuphine, all of which are weak antagonists of the μ opioid receptor and partial agonists of the κ opioid receptor, as well as being strong analgesics.

Another suitable agent for use with the invention are serotonin receptor agonists such serotonin 5 HT1a receptor agonists, which include by way of illustration and not limitation, 8-[4-[4-(2-pyrimidinyl)-1-piperazinyl]butyl]-8-azaspiro[4.5]decane-7,9-dione, also referred to as flesinoxan; and so forth. Preferred serotonin 5 HT1a receptor agonists include buspirone, which is commercially available as a salt having the formula:

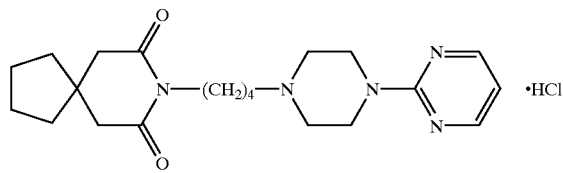

The α2-adrenoreceptor agonists suitable for use in the methods of the invention, include by way of illustration and not limitation, dexmedetomidine; detomidine; medetomidine; clonidine; bromonidine; tizanidine; mivazerol; guanfacine; oxymetazonline; (R)-(−)-3'-(2-amino-1-hydroxyethyl)-4'-fluoro-methanesulfoanilide; 2-[(5-methylbenz-1-ox-4-azin-6-yl)imino]imidazoline; 5-bromo-N-(4,5-dihydro-1H-imidazol-2-yl)-6-quinoxalinamine; 5,6,7,8-tetrahydro-6-(2-propenyl)-4H-thiazolo[4,5-d]azepin-2-amine; 6-ethyl-5,6,7,8-tetrahydro-4H-oxaazolo[4,5-d] azepin-2-amine; and 5,6-dihydroxyl-1,2,3,4-tetrahydro-1-naphyl-imidazoline.

A particularly useful combination of anti-thermoregulatory response agents is the κ opioid/μ opioid receptor agonist meperidine administered in combination with the α2-adrenoreceptor agonist dexmedetomidine.

The non-opiod analgesic monoamine uptake inhibitors suitable for use in the methods of the invention, include by way of illustration and not limitation, nepofam and tramadol.

The neuropeptides suitable for use in the methods of the invention, include by way of illustration and not limitation, neurotensin; neurotensin analogs; bombesin; neuromedin; dermorphin; and D-ala-deltorphin.

As noted above, pharmaceutically acceptable salts of the anti-thermoregulatory response agent are also well suited for use in the methods of the invention. These include, chlorpromazine hydrochloride, mesoridazine mesylate, acetophenazine maleate, fluphenazine decanoate, fluphenazine enanthate, prochlorperazine maleate, loxapine succinate, haloperidol lactate, haloperidol decanoate, amantadine hydrochloride, bromocriptine mesylate, apomorphine hydrobromide, trans-3,4-dichloro-N-methyl-N-[2-(1-pyrrolidinyl)cyclohexyl]benzene acetamide methanesulfonate, ethyl ketazocine methanesulfonate, nalbuphine hydrochloride, buspirone hydrochloride, dexmedetomidine hydrochloride, and so forth, along with mixtures thereof.

As indicated above, combinations of the aforementioned anti-thermoregulatory response agents are also contemplated. Exemplary combinations include a dopamine receptor blocker in combination with a κ opioid receptor agonist, and a dopamine receptor blocker in combination with an opioid agonist-antagonist analgesic. Specific examples of such exemplary combinations include trans-3,4-dichloro-N-methyl-N-[2-(1-pyrrolidinyl)cyclohexyl]benzene acetamide, its methanesulfonate salt, or (5a,7a,8B)-N-methyl-N-[7-(1-pyrrolidinyl)-1-oxaspiro(4,5)-dec-8-yl] benzene acetamide, in combination with chlorpromazine or thorazine; and nalorphine, pentazocine, buprenorphine, butorphanol, nalbuphine, cyclazozine, dezozine or nalorphone in combination with chlorpromazine or thorazine. A preferred combination is that of a dopamine receptor blocker and an opioid agonist-antagonist analgesic, preferably chlorpromazine or thorazine with nalbuphine or nalbuphine HCl. Accordingly, the invention also encompasses a composition for inhibiting a patient's thermoregulatory responses, comprising a dopamine receptor blocker and an opioid agonist-antagonist analgesic, or a pharmaceutically acceptable salt thereof, in combination with a pharmaceutically acceptable carrier.

Another suitable combination for use in the methods of the invention is described in Adler, et al., supra and comprises a synergistic combination of a κ opioid receptor agonist and a dopamine receptor blocker or dopamine receptor agonist. A third agent may also be included in this combination to enhance the activity of the κ opioid receptor agonist. This optional agent is a μ opioid receptor antagonist, for example, naloxone, naioxone hydrochloride, naltrexone and levallorphan methyl iodide salts, which have greater selectivity for μ receptors than other receptor types. In this manner, any μ receptor agonist properties of a κ opioid receptor agonist can be blocked or reversed with minimal effect on the κ opioid receptor agonist activity of the drug. Suitable dosages of a μ opioid receptor antagonist are within the range of about 50 μg–1 g. These μ opioid receptor antagonists are also useful if it is desired to quickly stop the hypothermia inducing method of the invention. Along with removal of the heat exchange device, a μ opioid receptor antagonist can be administered to effectively block or reverse the effect of the anti-thermoregulatory response agents of the invention.

Yet another example of a suitable combination is the use of an α2-adrenoreceptor agonist administered in combination with a neuropeptide.

Dosage of Anti-thermoregulatory Response Agents

A therapeutically effective amount of anti-thermoregulatory response agent is to be administered, which is intended to be a dosage sufficient to reduce or eliminate shivering in the patient being treated. The actual dosage amount will vary depending upon the patient's age and weight, along with the dosage form and anti-thermoregulatory response agent selected. Generally a typical dosage will be within the range of about 0.5 to 10 mg/kg of body weight, preferably about 0.5 to 2.0 mg/kg of body weight, and most preferably about 0.5 to 1.0 mg/kg of body weight of each component agent.

The preferred dosage will be dependent upon the time period during which the patient's body temperature is being reduced (either from a fevered state to normothermic or from normothermic to a hypothermic state), along with the actual drop in patient temperature that will be experienced during this procedure. Accordingly, for the methods of the instant invention, the amount of anti-thermoregulatory response agent administered should be sufficient to reduce shivering and/or inhibit vasoconstriction while the body temperature is being reduced and maintained at the lower temperature, which may be 24–72 hours.

It is important to note that the amount of anti-thermoregulatory response agent required for maintaining a patient at a predetermined temperature without shivering or vasoconstriction may be different than the amount required when the patient's temperature is being lowered to reach a predetermined temperature. For example, a patient may require a different dose of an anti-thermoregulatory response agent, generally more, to prevent shivering during active cooling than the dose needed to prevent shivering or vasoconstriction while being maintained at the target temperature. For this reason, it may be desirable to monitor the level of patient shivering, as shown in FIG. 23, so that the administration of anti-thermoregulatory response agent can be adjusted accordingly. Another factor to consider when selecting a dosage is the rate at which the temperature of the patient is being changed, i.e. the rate of cooling, since this may affect the shivering response and thus the dose of anti-thermoregulatory response agent that is appropriate. Likewise, the shivering response may be different at different temperatures below the shivering threshold. For example, a patient might shiver more vigorously at 34° C. than at 32° C. Additionally, of course, individuals will vary widely in their shivering thresholds, the vigor of their shivering response, and their sensitivity to the agent. The various agents may also vary in strength depending on their individual purity and preparation, and may vary to some degree between agents even in the same category. For all these reasons, dosage recommendations herein are merely suggestive and by no means comprehensive or restrictive.

It is believed that 0.1 mg to 5.0 g of anti-thermoregulatory response agent or combination of anti-thermoregulatory response agents will provide a therapeutic effect in the methods of the invention. Suitable dosages of a κ opioid receptor agonist range from about 0.1 mg to 5.0 g, while suitable dosages of a dopamine blocker or dopamine agonist range from about 0.1 mg to 3.0 g. Suitable dosages of a serotonin 5 HT1a receptor agonist range from about 10 mg to 50 mg.

For a combination of a κ opioid receptor agonist and a dopamine receptor blocker or dopamine agonist, a particularly suitable dosage is about 4–40 parts by weight of κ opioid receptor agonist per 1 part by weight of dopamine blocker or dopamine agonist. Suitable dosages of an opioid agonist-antagonist analgesic range from about 0.1 mg to 5.0 g. For a combination of a an opioid agonist-antagonist analgesic and a dopamine blocker, a particularly suitable dosage is about 1 to 40 parts by weight of an opioid agonist-antagonist analgesic per 1 part by weight of a dopamine blocker.

Route of Administration of Anti-thermoregulatory Response Agents

There are numerous routes and formulations by which the anti-thermoregulatory response agent can be administered to the patient undergoing the hypothermia inducing procedures described herein. For example, the anti-thermoregulatory response agent can be administered either alone or in combination with other pharmaceutically acceptable excipients, including solid, semi-solid, liquid or aerosol dosage forms, such as, for example, tablets, capsules, powders, liquids, injectables, suspensions, suppositories, aerosols or the like. The anti-thermoregulatory response agent can also be administered in sustained or controlled release dosage forms, including depot injections, osmotic pumps, pills, transdermal (including electrotransport) patches, and the like, for the prolonged administration of the anti-thermoregulatory response agent at a predetermined rate. The compositions will typically include a conventional pharmaceutically acceptable carrier or excipient and the anti-thermoregulatory response agent or a pharmaceutically acceptable salt thereof. In addition, the composition may include other medicinal agents, pharmaceutical agents, carriers, adjuvants, and so forth. Generally, depending on the intended mode of administration, the pharmaceutically acceptable composition will contain about 0.1–90.0% by weight, preferably about 0.5–50.0 wt %, of the anti-thermoregulatory response agent or its salt, the remainder being suitable pharmaceutical excipients, carriers, etc. See, for example, "Remington's Pharmaceutical Sciences" (Mack Publishing Company, Pennsylvania, 18th Edition, 1990) and "Goodman & Gilman's the Pharmacological Basis of Therapeutics", (Goodman, et al., Eds., 9th edition, 1996) for extensive discussions on the preparation and composition of various formulations suitable for use in administering the anti-thermoregulatory response agents described herein.

The anti-thermoregulatory response agent can be administered orally, transdermally, directly into the cerebrospinal fluid (e.g., intracereboventricualrly or intracisternally) or parenterally (intramuscularly or intravenously), with intramuscular or intravenous injection being the preferred routes of administration.

For oral administration, the compositions may take the form of a solution, suspension, tablet, capsule, powder, sustained release formulation, and the like. A typical pharmaceutically acceptable composition is formed by the incorporation of any of the normally employed excipients, such as, for example, a diluent (lactose, sucrose, glucose, dicalcium phosphate), lubricant (magnesium stearate), disintegrant (crosscarmellose sodium), binder (starch, gum acacia, polyvinylpyrrolidone, gelatin, cellulose, cellulose derivatives), mannitol, povidone, sodium saccharine, talcum, magnesium carbonate, and the like. Such compositions take the form of solutions, suspensions, tablets, dispersible tablets, pills, capsules, powders, sustained release formulations and the like.

Liquid pharmaceutically administrable compositions can, for example, be prepared by dissolving or dispersing an anti-thermoregulatory response agent and optional pharmaceutical adjuvants in a carrier, such as, for example, water, saline, aqueous dextrose, glycerol, glycols, ethanol, and the like, to thereby form a solution or suspension. If desired, the pharmaceutical composition may also contain minor amounts of nontoxic auxiliary substances such as wetting agents, suspending agents, emulsifying agents, or solubilizing agents, pH buffering agents and the like, for example, sodium acetate, sodium citrate, cyclodextrine derivatives, polyoxyethylene, sorbitan monolaurate or stearate, triethanolamine oleate, etc. Liquid or semi-solid oral formulations can also be prepared by dissolving or dispersing the anti-thermoregulatory response agent or its salt in vegetable oils, glycols, triglycerides, propylene glycol esters (e.g. propylene carbonate) and the like, and encapsulating these solutions or suspensions in hard or soft gelatin capsule shells to provide a solid dosage form.

Formulations for parenteral injection can be prepared in conventional forms, either as liquid solutions or suspensions, solid forms suitable for solution or suspension in liquid prior to injection, or as emulsions. Formulations of 0.1 to 10 wt % anti-thermoregulatory response agent in solution are acceptable, with 2.5 wt % being typical.

Timing of Administration of the Anti-thermoregulatory Response Mechanism

When inducing hypothermia, it is preferred to have therapeutic levels of the anti-thermoregulatory response agent in the blood stream or maintenance of the skin temperature already established by warming the skin, while the heat exchange device is being used to lower the patient's core temperature. Accordingly, the preferred methods of the invention contemplate administration of the anti-thermoregulatory response mechanism prior to initiation of the cooling step. When controlling the rate of heating of an already hypothermic patient, or when maintaining hypothermia at a stable temperature below the shivering threshold, it is also preferable to have therapeutic levels of the anti-thermoregulatory response agent in the blood stream or the skin temperature already being maintained by warming the skin. When using anti-thermoregulatory response agents, this can be accomplished by administering a bolus dosage to achieve the desired therapeutic level of anti-thermoregulatory response agent in the blood, which can then be subsequently maintained by periodic or continuous administering the agent. The agent may be administered periodically at a larger dose, for example intramuscular, or can be administered continuously at a smaller dose, for example intravenously.

The anti-thermoregulatory response mechanism may be administered prior to positioning the heat exchange device, before the cooling step commences, simultaneous with the cooling step, which can commence at the time the device is inserted or applied externally to the patient or at the time that the heat exchange device is activated, or at a point in time subsequent to the initiation of the cooling step. Yet another embodiment contemplates continuing to administer the anti-thermoregulatory response mechanism for some time after the heat exchange device has ceased to operate. As noted above, a single one-time dosage of agent or application of warmth, several periodic dosages of agent or application of warmth administered at set time intervals, continuous administration of agent or warmth, or a combination of these are also contemplated. The actual timing of administration of the anti-thermoregulatory response mechanism is best illustrated in FIG. 23, which shows the numerous points at which the anti-thermoregulatory response mechanism can be administered, either sequentially or simultaneously with the other steps in the methods of the invention.

Appropriate dosages and means and timing of administration may vary dramatically between individuals and in various medical situations. Often the physician will need to titrate the anti-thermoregulatory response agent to the individual and the situation. Additional appropriate dosages and specific drug administration regimes are set out in the section below concerning the treatment of specific conditions.

Heat Exchange System

The heat exchange system includes preferably a heat exchange catheter, a controller, and an external heat exchanger. The catheter preferably comprises at least one fluid lumen through which a thermal exchange fluid may be circulated, a heat exchanger and a working lumen extending from outside the patient through at least part of the catheter that is inserted into the patient. An example of such a catheter may be an elongate catheter having a proximal end and a distal end, where the entire length of said flexible catheter is defined as the distance from its proximal end to its distal end, and comprising at least one fluid lumen through which a thermal exchange fluid may be circulated, a heat exchanger with heat exchange fins located at a first location on the catheter, and a working lumen extending from outside the patient through at least part of the catheter that is inserted into the patient.

The heat exchanger operates to exchange heat between blood which flows in heat exchanging proximity to the heat exchanger and a thermal exchange fluid which is circulated through the catheter. The first location at which the heat exchanger is located may constitute less than the entire length of the catheter, and is typically at or near the distal end of the catheter. The heat exchanger may specifically comprise a balloon or other structure through which the thermal exchange fluid may circulate, and the heat exchange fins may be a plurality of lobes of the balloon or other surface area increasing projections such as outwardly extending protuberances, ribs, filaments of a multi-filament device, curved or undulating surfaces, etc., that enhance the efficiency with which heat exchange occurs. A suitable heat exchanger is the catheter described in greater detail below.

An external heat exchanger may be, for example, a thermoelectric heater/cooler over which the heat exchange fluid is circulated and which thereby controls the temperature of the heat exchange fluid.

The invention also contemplates a means for controlling the heat exchange system so that a predetermined temperature of the patient is established and maintained. For example, a control system can monitor body temperature and the system is then controlled in response to the body temperature. In this manner, the system can be modulated or shut off when the patient's body or target region reaches a pre-selected temperature, and similarly, can be modulated, for example turned on, when the temperature deviates from the pre-selected temperature.

Figure 24:
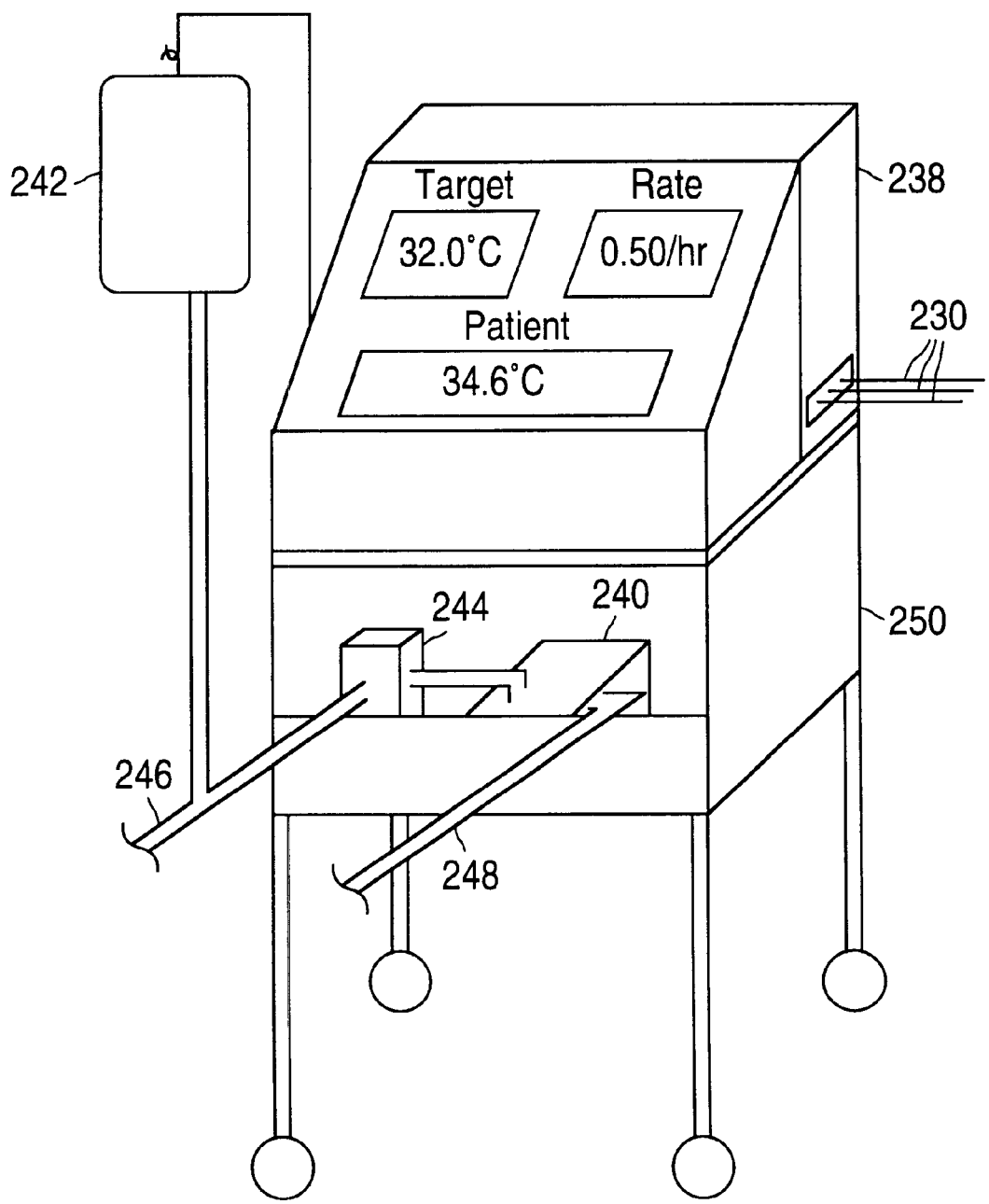
FIG. 24 is a front view of control system useful in the methods of the invention.
Figure 25:
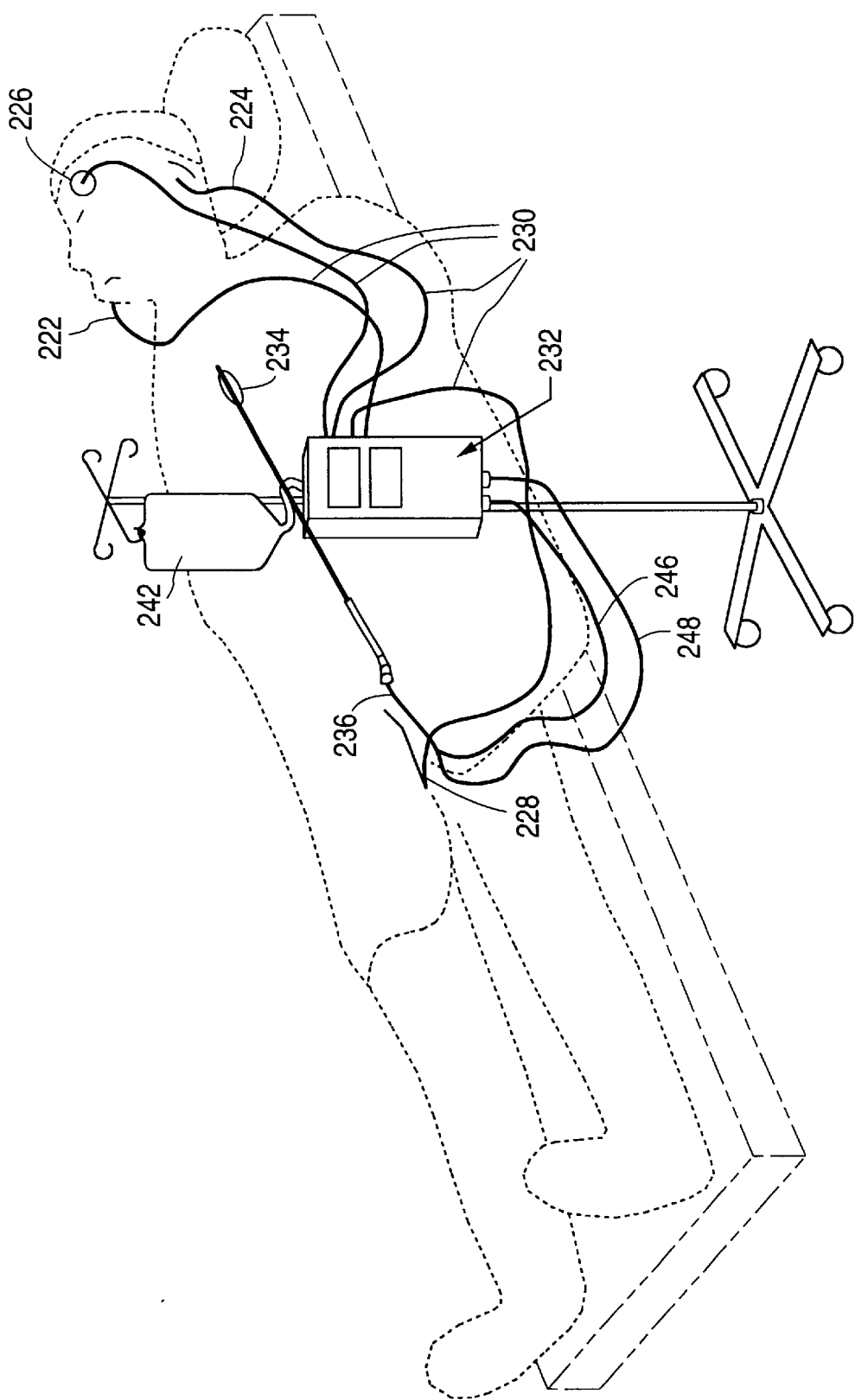
FIG. 25 illustrates a control system in operation.

A significantly more sophisticated and automatic control over temperature regulation is possible. Examples of such control systems are shown in FIG. 24 and FIG. 25. In the control system, feedback from the patient's body is obtained by one or more temperature sensors attached to the patient and directed to the controller. Examples include an esophageal temperature probe 222, a tympanic temperature probe 224, a skin temperature probe 226, a rectal temperature probe 228, or other appropriate sensors as is well known in the art. These probes generate signals that represent the temperature sensed and transmit those signals over a plurality of wires 230 to a control unit 232, one embodiment of which is illustrated in FIG. 25. The control unit receives the temperature signals and controls the heat exchange region 234 of the heat exchange catheter 236 in response thereto. The control unit may optionally also be used to control the anti-thermoregulatory response mechanism when the mechanism involves use of a warming device.

FIG. 25 illustrates another embodiment of a control unit 250 may include a programmable computer 238, a thermoelectric heater/cooler 240, a supply of heat exchange fluid 242, and a pump 244. The pump may pump the heat exchange fluid through the supply source, for example, a bag 242 over the thermoelectric heater/cooler to alter the temperature in the fluid. The fluid may be pumped from an inlet tube 246 received from the heat exchange catheter, through the bag and back to the heat exchange catheter through the outlet tube 248. In response to the temperature sensed, the controller may control the pump rate, or may control the temperature of the thermoelectric heater/cooler.

In one embodiment, the control unit is programmed to control the heat exchange catheter to reach and maintain a target temperature. The supply of heat exchange fluid is a closed loop of heat exchange fluid circulating through the catheter inside the patient and external of the patient through the bag of fluid positioned adjacent the thermoelectric heater/cooler. As the sensed temperature of the patient approaches the target temperature, the control unit may adjust the temperature of the thermoelectric heater/cooler to approach the target temperature. For example, if the computer was programmed to control the patient's temperature at 32° C., the thermoelectric cooler might originally be at a temperature of near 0° C., and thus the temperature of the heat exchange fluid flowing within the balloon would be about 0° C. However, as the temperature of the patient fell and began to approach 32° C., the control unit would act to increase the temperature of the thermoelectric heater/cooler (by altering the current flowing therethrough, for example) so that it began to warm toward 32° C. It has been found that a temperature of the heat exchange fluid of about 30° C. will remove approximately the amount of heat that a body at rest at 32° C. generates, so as the body temperature reaches the target temperature of 32° C., the control unit will gradually control the thermoelectric heater/cooler to level off at a constant temperature of 30° C. and thus control the temperature of the heat exchange fluid at about 30° C. It should be noted that when the patient is maintained at a constant temperature, the heat exchange system is not inactive, but is actually functioning to remove a certain amount of heat from the patient. The feedback system will likewise be active; if the patient begins to drop in temperature, the system may respond to add heat to the heat exchange fluid; of the temperature begins to rise, the system may respond to remove even more heat from the heat exchange fluid and thus the patient.

Similarly, the control unit may regulate the rate of temperature change. A rate of change of patient temperature may be programmed into the computer of the controller. If the sensed temperature of the patient is changing more rapidly or more slowly than the programmed rate, the temperature of the heat exchange fluid may be controlled by controlling the thermoelectric heater/cooler and thus removing or adding heat through the heat exchange catheter to the blood of the patient in appropriate amounts to control the rate of temperature change in the patient. It has been found that an uncontrolled patient may warm faster than desired. In such a situation, the controller may act to control the rate of temperature increase by actually removing heat from the blood, in effect cooling the patient so that the rate of warming is slowed to the desired rate.

It may be readily seen that many variations on this control unit are possible without departing from the invention. For example, the control unit may receive signals from one, two or more temperature sensors, which would be included in the control system. Sensors of other parameters than body temperature, such as pulse rate or blood pressure or the like, are within the contemplation of the invention, and may also be included in the control system. Likewise, the target temperature is only one end point that may be desirable with the controller; the target may be some other bodily condition such as blood pressure, EEG condition, and the like. Also the nature of the response of the control unit which serves to control the heat exchanger may vary. It may be a simple as an on/off response. It may vary the rate of pumping, the temperature of the thermoelectric plate, or any other suitable variable to control the heat exchanger.

Kits

Another aspect of the invention pertains to a kit for controlling the temperature of a patient comprising (a) a heat exchange device and (b) an anti-thermoregulatory response mechanism. The kit may contain instructions, as appropriate, both as to the operation of the device and the anti-thermoregulatory response mechanism. When the anti-thermoregulatory response mechanism is one or more anti-thermoregulatory response agents, the kit may also include information pertaining to the storage and dosage instructions for the anti-thermoregulatory response agent(s), and so forth For example, the kit may contain instructions for the proper insertion of the catheter into the vascular system as is well known in the medical arts, for example by the Seldinger technique. The instructions may also contain a description of the proper use of the heat exchange catheter system, the proper target temperature for the patient, and if the kit contains a control unit, the appropriate ramp rates for heating and cooling the patient, as well as specific recommendations for the use of the anti-thermoregulatory response mechanism. The kit may or may not contain the anti-thermoregulatory response mechanism, but may contain a description of the preferred anti-thermoregulatory response mechanism, for example a preferred anti-thermoregulatory response agent or combination of agents selected from those set out above, and suggestions as to dosage and methods of administration and the like. The duration of administration of cooling and use of the anti-thermoregulatory response mechanism may also be set out.

In one embodiment of the kit, the heat exchange device is a catheter. A suitable catheter is an elongate catheter having a proximal end and a distal end, the entire length of the catheter being defined as the distance from its proximal end to its distal end, and comprises (i) at least one fluid lumen through which a thermal exchange fluid may be circulated; (ii) a heat exchanger with heat exchange fins located at a first location on the catheter; and (iii) a working lumen extending from outside the patient through at least part of the catheter that is inserted into the patient.

The kit can optionally include a control system that monitors body conditions, for example by measuring temperature, and controls the heat exchange device in response to the body conditions being monitored, such as turning off the device when the patient's body or target region reaches a pre-selected temperature, or reactivating the device when the temperature deviates from the preselected temperature. In addition, the kit may also comprise a second heat exchange device. This second device may serve to compliment the temperature lowering ability of the first device, i.e., the second device may also serve to lower the temperature of the body or portion thereof. Alternately, the second device may serve to increase the temperature of the patient's body or body portion. This is useful to provide heat in the event that the method of the invention results in a lower temperature than is desired, or if it is desired to conclude the therapy and raise the patient's temperature to normothermic.

These and other methods of the invention are readily understood in references to the figures described below. One embodiment of the heat exchange device suited for use in the methods of the invention is illustrated in FIG. 1, which shows the distal end 2 of a heat exchange device 4, which has been inserted through the patient's skin into a blood vessel 6. Blood flow through the vessel is indicated by a set of flow arrows. Preferably, the device is inserted into a relatively large blood vessel, e.g., the inferior or superior vena cava, a femoral artery or vein, a jugular artery or vein, or the aorta. Use of these vessels is advantageous in that they are readily accessible, provide safe and convenient insertion sites, and have relatively large volumes of blood flowing through them. In general, large blood flow rates facilitate more efficient heat transfer between the catheter and the blood. For example, the jugular vein may have a diameter of about 22 French, or a bit more than 7 mm, where 1 French is 0.013 inches or 0.33 mm. A heat exchange device suitable for insertion into a vessel of this size can be made quite large relative to devices intended for insertion into smaller vessels in the vascular system.

A particularly well suited heat exchange device is a catheter. Atherectomy or balloon angioplasty catheters, used to clear blockages from the coronary artery and similar vessels, commonly have external diameters in the range between 2 to 8 French. In contrast, it is anticipated that a catheter useful in the methods of the instant invention will typically have an external diameter of about 9 French, although this dimension may obviously be varied a great deal without departing from the basic principles of the claimed invention. It is desirable that the catheter or other heat exchange device be small enough so that the puncture site can be entered using the percutaneous Seldinger technique, a technique well known to medical practitioners. Other techniques for inserting devices into the above mentioned blood vessels are also well known among medical personnel.

Although a small diameter is chosen for the heat exchange device, this diameter is based upon the pre-insertion size, and is aimed at avoiding or minimizing vessel trauma. However, after the device is inserted in the vessel, its distal end can be expanded to any size so long as blood flow is not unduly impeded. Additionally, the femoral artery and vein and the jugular vein are all relatively long and straight blood vessels. This will allow for the convenient insertion of a device having a temperature controlled region of considerable length. This is of course advantageous in that more heat may be exchanged at a given temperature for a device of a given diameter if the length of the heat transfer region is increased. Although the method of the present invention will probably be most commonly employed in a hospital, the procedure need not be performed in an operating room. The method and apparatus are so simple that the device may be inserted and treatment to lower the patient's temperature and reduce shivering may begin even in an ambulance or in the field.

In general, the distal end 2 of the device may be cooled and maintained at a temperature below the patient's body temperature. Blood flowing through the vessel will therefore be cooled, and will then be circulated rapidly throughout the patient's circulatory system. The beneficial effect of cooling the patient's blood in the vicinity of the device will thereby be spread very quickly throughout the entire body of the patient.

The device depicted in FIG. 1. can utilize a variety of cooling methods and can have numerous configurations that maximize its heat exchanging capability. A particularly well suited heat exchange device is a catheter, several configurations of which are described in detail in Ginsburg, U.S. Pat. No. 5,486,208 and Ginsburg, WO 98/26831, the disclosures of which are incorporated herein by reference. For example the catheter can have a thermally conductive shaft running the length of the catheter body, made of a metal or other material having a high thermal conductivity. By cooling the proximal end of the shaft with an external cooling apparatus, heat will be caused to flow either into the distal end of the shaft. Another cooling mechanism is provided by a catheter having two lumens running through it. Fluid flows from the proximal end of the catheter through in-flow lumen, through a heat transfer region, and back out through an out-flow lumen. By supplying cooled fluid through the inflow lumen, heat may be transferred from the patient's blood stream. Other embodiments and modifications for heat transfer other than by use of a heat exchanging fluid, e.g., resistance, including radio frequency, will occur to those skilled in the art.

The heat exchange devices useful in the methods of the invention are preferably designed to optimize the rate of heat transfer between the device and the body, tissue or fluid, for example with blood flowing through the vessel. While a large surface area is desirable in order to increasing the effective heat transfer, care must be taken so that the device does not unduly restrict blood flow through the vessel. The device can be fitted with a plurality of protrusions to maximize the heat transfer surface area, such as heat transfer vanes, radial fins or longitudinal fins, or a multi-lobed balloon surface, collectively referred to as heat exchange fins. In addition, the heat transfer region of the device can be in the form of an expandable balloon, where the balloon remains inflated by, for example, the pressure difference in a fluid flows through an inflow and outflow lumen.

It is estimated that heat exchange device whose surface temperature is controlled between about 1 to 15° C. and may provide a body core cooling rate of approximately 6 to 8° C. per hour in a patient of typical size, for example 115 pounds to 195 pounds and having approximately normal body temperature (37° C.). This estimate is highly dependent on a number of factors including the rate of blood flow through the vessel, the initial body temperature of the patient, the external surface area of the device through which heat is transferred, etc. The actual rate achieved may vary substantially from the above estimate. A more helpful estimation of temperature control of the patient's body may be the wattage of energy [heat] removed from the body. At normal blood flows over a catheter as described, as many as 300 watts of energy may be removed from the blood. At rest, the human body generates about 100 watts, but shivering may increase this amount to as much as five-fold. The ability to cool the body or control the body's temperature is thus greatly enhanced by the administration of anti-thermoregulatory response agents while employing the cooling catheter. Other design considerations include a sensitive temperature sensor (see for example, FIG. 23) to closely monitor the temperature of the distal end of the device. While care should be taken to avoid freezing the tissue or fluid or inducing shock to the patient, this is rarely a concern. Since blood is essentially water containing a number of suspended and dissolved substances, its freezing point is somewhat below 0° C.

As may be readily appreciated, the rate of temperature alteration of the patient is greatly dependent on the amount of heat being removed from the blood. This in turn is greatly dependent on the difference in temperature between the blood and the surface of the heat exchange device ($\Delta T$). When it is desirable to rapidly cool the patient, the temperature of the device will be as cold as possible, for example by cooling a heat exchange fluid to almost 0° C., whereas when the operator wants the patient's temperature to remain constant, for example after a state of hypothermia has been reached, only the amount of heat generated by the body in excess of that which is normally lost to the environment needs to be removed. Thus it may be that the temperature of the balloon surface may be maintained near 0° C. during cooling, and as the body reaches the required hypothermic level, the temperature of the heat exchange surface may be maintained just a few degrees below body temperature, for example at about 30° C. once the hypothermic state of 32° C. has been reached.

In heating, it is conservatively accepted that a temperature of a device in contact with the blood may be 42° C. without causing injury to the blood. The $\Delta T$ in warming then will generally be less than when the heat exchanger is cooling the blood. If a carefully controlled rate of warming is desired, it will be readily appreciated that a large amount of metabolic heat generated by the body by shivering may overwhelm the system's ability to precisely control the rate of warming. Therefore even when warming a hypothermic patient, control of shivering is important.

Some preferred configurations of heat exchange devices are illustrated in the accompanying figures. In FIG. 2, a heat exchange balloon catheter 10 with a finned balloon portion 12 may be positioned within at least a portion of the descending aorta 14 and a blood vessel 16 conducting blood flow to the brain region. The balloon portion 12 is typically formed of material that is sufficiently thin to promote effective thermal transfer between heat exchange fluid within the balloon and blood flowing within heat exchange proximity of the balloon, but which is not excessively elastic to expand and unintentionally obstruct a fluid passageway or blood vessel 16. A particularly suitable material is a thin, strong but relatively inelastic material such as PET (polyethylene terephthalate), which will allow for a predictable balloon configuration with adequate heat exchange properties. The catheter shaft 18 of the thermal catheter 10 may be placed in a desired location relative to a selected body region or artery 16 by conventional techniques such as guiding catheters or steerable wire over-the-wire technique as known to those of ordinary skill in the field. The balloon portion 12 of the catheter 10 may support the closed-loop circulation of a heat transfer fluid within the catheter and balloon as described in the example set forth below. The increased surface area of the inflated balloon may provide effective heat transfer within a body region by thermal conduction, and the configuration of the balloon may further permit continued blood flow without substantial disruption by creating channels exterior of the balloon surface when the balloon is expanded.

FIG. 3 illustrates a heat exchange balloon 12 mounted on a shaft 18, the balloon being defined by a longitudinal axis and a plurality of heat transfer fins 20, 22, 24 and 26 projecting radially outward from the longitudinal axis of the catheter shaft. The heat transfer fins may be formed, for example, as the lobes of a multi-lobed, collapsible balloon. The shaft 18 is generally round and in this embodiment includes a working lumen 28 running through the shaft and open at the distal end of the catheter. Although in a preferred method, the anti-thermoregulatory response agent is administered by intramuscular or intravenous injection, it may also be administered through the central, or working lumen In one embodiment of the invention, the working lumen is used for the injection of the anti-thermoregulatory response agent. The working lumen can also serve other functions. For example, along with being provided in combination with an anti-thermoregulatory response agent, the catheter device may further be provided in combination with a device (such as a guide wire, or embolectomy catheter) or other medicament (such as a thrombolytic agent, a barbiturate, an anticoagulant, a neuroprotectant, an anti-seizure agent, an oxygenated perfusate, a vasodilator, an agent which prevents vasospasm, an agent to prevent platelet activation, and an agent to deter the adhesion of platelets), all of which can be insertion through the working lumen. In addition, the working lumen may be used for the injection of fluoroscopic dye, for the receipt of a guide wire, or as a guiding catheter for various diagnostic or therapeutic devices including, for example, an angioplasty catheter, an embolectomy catheter, an occlusion member delivering catheter, an embolization member delivering catheter, an electro-cautery device, or a microcatheter. As may be appreciated, the use of the lumen for one function does not prevent its subsequent use for another, so it may be used sequentially for several or even all of the uses described here.

The shaft exterior of the central lumen is shown in FIG. 4 and FIG. 6 as being divided by a web 30 into two channels, an inlet channel 32 and an outlet channel 34. The shaft has inlet orifices 36, 38, 40 (shown in FIG. 3) communicating between the inlet channel and the interior of the balloon at the distal portion of the balloon. The shaft also has outlet orifices 42, 44, 46 communicating between the interior of the balloon and the outlet channel. A plug 48 is inserted in the outlet channel between the inlet and the outlet orifices.

The balloon 12 may be made of, for example, a single sheet of collapsible thin plastic material 50, as shown in FIG. 5 sufficiently thin to allow for effective thermal exchange between a heat exchange fluid on the interior of the balloon and blood flowing over the exterior of the balloon. Tacking the material to the shaft as shown at 52 may form lobes of the balloon. Tacking the sheet of plastic to itself in appropriate locations as shown at 54 and 56 may further shape the lobes. The lobed shape of the balloon surface provides a significant surface area for heat exchange while also providing for continued flow past the balloon through the space between the lobes of the balloon.

In operation, heat exchange fluid (not shown) is pumped under pressure into the inlet channel 32. Suitable heat exchange fluids include, by way of illustration and not limitation, sterile saline or other biocompatible fluid with appropriate heat transfer characteristics. The heat exchange fluid flows down the inlet channel until it reaches the inlet orifices 36, 38, 40 at the distal end of the balloon. The fluid flows from the inlet channel into the interior of the balloon. It then flows in a proximal direction through the interior of the balloon until it reaches the outlet orifices 42, 44, 46 at the proximal end of the balloon. The heat exchange fluid then flows from the interior of the balloon through the outlet orifices and into the outlet channel 34 where it then flows back down the shaft and out of the body. In this manner, the heat exchange fluid absorbs heat from the blood flowing in heat transfer proximity to the balloon.

Figure 7:
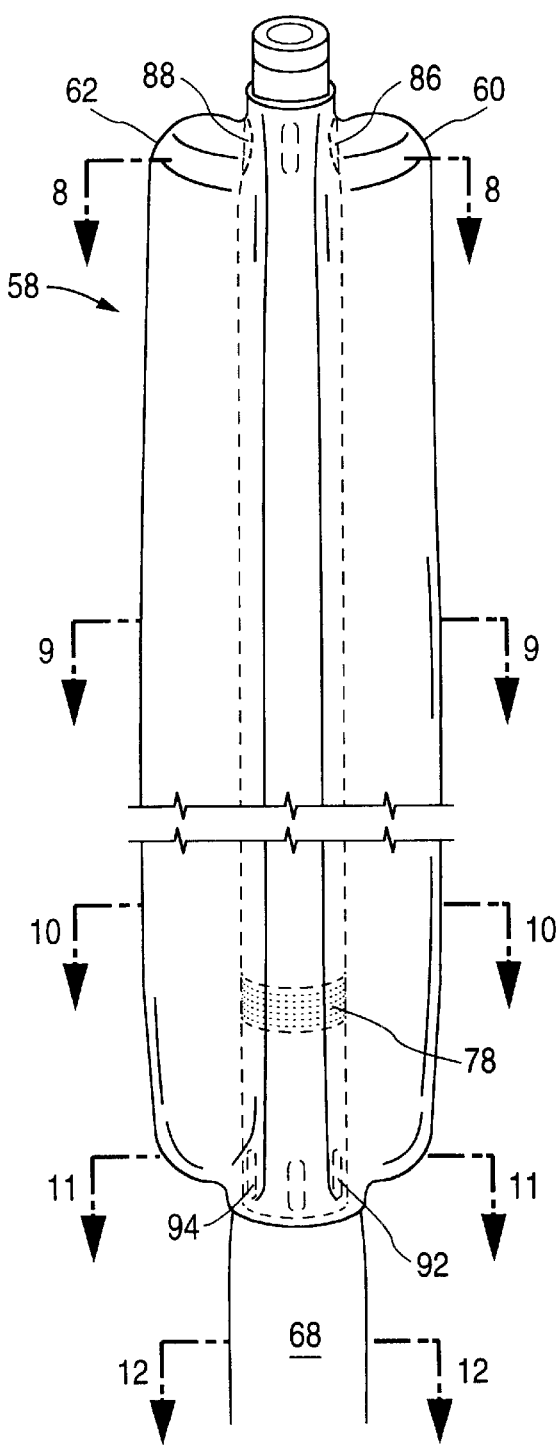
FIG. 7 illustrates an alternative construction of a heat exchange catheter.
Figure 12:
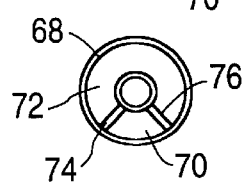
FIG. 12 is a cross-sectional view of the proximal shaft of the catheter taken along line 12—12 of FIG. 7.

An alternative construction to the heat exchange balloon is shown in FIG. 7 wherein the heat exchange region is formed using a series of three collapsible balloon lobes 60, 62, 64 located around a central collapsible lumen 66. A proximal shaft 68 is formed having two channels, an inlet channel 70 and an outlet channel 72. The interior of the shaft is divided into two lumens by webs 74 and 76, as shown in FIG. 12, but the lumens do not occupy equal portions of the interior of the shaft. The inlet channel occupies about ⅓ of the circumference of the interior; the outlet channel occupies about ⅔ of the circumference of the interior for reasons that will be explained below.

Figure 8:
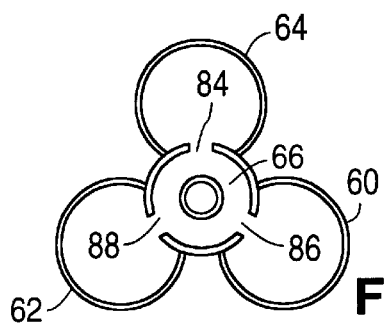
FIG. 8 is a cross-sectional view of the distal end of the catheter taken along line 8—8 of FIG. 7.
Figure 9:
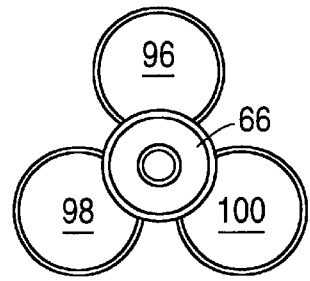
FIG. 9 is a cross-sectional view of a portion of the central section of the catheter taken along line 9—9 of FIG. 7.
Figure 10:
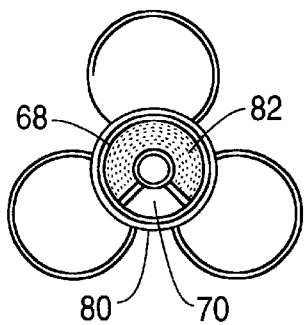
FIG. 10 is a cross-sectional view of another portion of the central section of the catheter taken along line 10—10 of FIG. 7.
Figure 11:
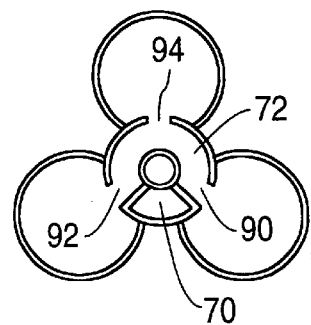
FIG. 11 is a cross-sectional view of the proximal end of the catheter taken along line 11—11 of FIG. 7.

At the heat exchange region of the catheter, a transition 78 is formed between the shaft 68 and the tube 80 forming the central collapsible lumen 66. The outlet channel is plugged 82, as shown in FIG. 10, the tube 80 is affixed over the shaft 68 by, for example gluing, at the transition 78, and the shaft ends with the tube (not shown). In this way, as shown in FIG. 9, the inlet channel in this portion of the catheter occupies the entire circumference of the shaft. At the distal end of the balloon, shown in FIG. 8, inlet orifices 84, 86, 88 are formed between the inlet channel and the three collapsible balloons. At the proximal end of the heat exchange region, shown in FIG. 11, outlet orifices 90, 92, 94 are formed between the interior of each balloon and the outlet channel in the shaft. The configuration of the outlet channel is such that communication with the interior of each of the three balloons is possible.

In operation, heat exchange fluid flows down the inlet channel in the shaft 70, continues down lumen 66 to the distal end of the heat exchange region, exit the lumen through the inlet orifices 84, 86, 88 to the interior lumens of the balloon lobes 96, 98, 100, travel back down each of the three balloons and re-enter the shaft through the outlet orifices 90, 92, 94 and then down the outlet channel 72 toward the proximal end of the catheter. In this way heat exchange fluid may be circulated through the three balloons to remove heat from the blood flowing in heat transfer proximity to the balloons. The material from which the balloons are made is made of a material that will permit significant thermal exchange between the heat exchange fluid on the interior of the balloon and the body fluid such as blood flowing in heat exchange proximity to the surface of the balloon. A particularly suitable material is very thin plastic material, which may also be made strong enough to withstand the pressure necessary for adequate flow of the heat exchange fluid.

FIG. 13 illustrates another heat exchange catheter 102 suitable for use in the method of this invention. The catheter 102 is constructed by attaching a balloon 104 having multiple lumens, over an inner shaft member 106 in the manner described below. The assembled catheter 102 (FIG. 13) has a four-lumen thin-walled balloon 104 (FIG. 15) which is attached over an inner shaft 106 (FIG. 14).

The cross-sectional view of the four-lumen balloon taken along line 16—16 of FIG. 15 is shown in FIG. 16. The four-lumen thin-walled balloon 104 has three outer lumens 108, 110 and 112, which are wound around an inner lumen 114 in a helical pattern. All four lumens are thin walled balloons and each outer lumen shares a common thin wall segment (116, 118, 120) with the inner lumen 114. The balloon is approximately twenty-five centimeters long and when installed, both the proximal end 122 and the distal end 124 are sealed around the shaft 106 in a fluid tight seal.

The shaft 106 is attached to a hub 126 at its proximal end. The cross-sectional view of the proximal shaft at line 17—17 in FIG. 14 is shown at FIG. 17. The interior configuration of the shaft has three lumens: a guide wire lumen 128, an inflow lumen 130 and an outflow lumen 132. It is understood however, the lumens 130 and 132 are referred to as inflow and outflow for illustrative purposes only. One of skill in the art may readily appreciate that lumen 132 may be used as the inflow lumen and lumen 130 may be used as the outflow lumen if the flow of the heat exchange fluid is reversed.

At the hub 126, the guide wire lumen 128 communicates with a guide wire port 134, the inflow lumen 130 is in fluid communication with an inflow port 136, and the outflow lumen 132 is in communication with an outflow port 138. Attached at the hub 126 and surrounding a portion of shaft 106 is a length of strain relief tubing 140 which may be, for example, shrink tubing.

Between the strain relief tubing 140 and the proximal end 122 of the balloon, the shaft 106 is at the extruded outer diameter of about 0.118 inches. The internal configuration is as shown in FIG. 17. Immediately proximal of the balloon attachment at its proximal end 22, the shaft has a necked down section 142. The outer diameter of the shaft is reduced to about 0.10 to 0.11 inches, but the internal configuration of the lumens is maintained. Compare, for example, the shaft cross-section shown in FIG. 17 with the cross-section shown in FIG. 18 or the shaft cross-section shown in FIG. 20. This length of reduced diameter shaft remains at approximately constant diameter between the first necked down section 142 and a second necked down section 144.

Immediately distal of the necked down section 142, a proximal balloon marker band 146 is attached around the shaft. The marker band 146 is a radiopaque material such as a platinum band or radiopaque paint, and is useful for locating the proximal end of the balloon by means of fluoroscopy while the catheter is within the body of the patient.

At the marker band 146, the distal end of all four lobes of the balloon (108, 110, 112, 114) at 122 are fastened to the inner member 122. This may be accomplished by folding the balloon down around the shaft, placing a sleeve, for example a short length of tubing, over the balloon and inserting adhesive, for example by wicking the adhesive around the entire inner circumference of the sleeve. This simultaneously fastens the balloon down around the shaft, and creates a fluid tight seal at the proximal end of the balloon.

Distal of this seal, under the balloon, a window 148 is cut through the wall of the outflow lumen in the shaft. Juxtaposed to that window, a plurality of slits 150 are cut into the wall of the outer balloon lumen, as shown in the cross-sectional view of FIG. 18 and the view in FIG. 19. Because the outer lumens are twined about the inner lumen in a helical fashion, each of the outer tubes passes over the outflow lumen of the inner shaft member at a slightly different location along the length of the inner shaft, and where each of the other two outer lumens pass over the outflow lumen of the shaft, other windows (152, 154) are cut into the outflow lumen and a plurality of slits (156, 158) are cut into the outer lumen to fluidly connect the proximal portion of that outer lumen to the outflow lumen of the shaft. See, for example, the section of FIG. 13 immediately distal of line 18—18. In this way the proximal portion of each outer lumen (108, 110, 112) is fluidly connected to the outflow lumen of the shaft.

Distal of the windows in the outflow lumen, the inner lumen 114 of the four-lumen balloon is sealed around the shaft in a fluid tight seal. The outflow lumen 132 is plugged 160, and the wall to the inflow lumen is removed, as shown in FIG. 20. This may be accomplished by the necked down section 144 to seal the outflow lumen shut (plug 160), removing the wall 162 of the inflow lumen 130, and affixing the wall of the inner lumen of the balloon around the entire outside 164 of the shaft with adhesive. The adhesive will also act as a plug to prevent the portion of the inner lumen proximal of the plug from being in fluid communication with the inner member distal of the plug.

Just distal of the necked down section 144, the guide wire lumen 128 of the shaft may be terminated and joined to a guide wire tube 166. The tube 166 then continues to the distal end of the catheter. The inflow lumen 130 is open into the inner lumen of the four-lobed balloon and thus in fluid communication with that lumen.

The distal end 124 of the balloon 104 including all four lumens of the balloon is sealed down around the guide wire tube 166 in a manner similar to the way the balloon is sealed at the proximal end around the shaft. This seals all four lumens of the balloon in a fluid tight seal. Just proximal of the seal, a plurality of slits 168 are cut into the common wall between each of the three outer lumens 108, 110, 112, of the balloon and the inner lumen 144 so that each of the outer lumens is in fluid communication with the inner lumen, as is shown in FIG. 21 and the cross-sectional view of FIG. 22.

Just distal of the balloon, near the distal seal, a distal marker band 170 is placed around the inner shaft. A flexible length of tube 172 may be joined onto the distal end of the guide wire tube 166 to provide a flexible tip to the catheter. The distal end 174 of the flexible tube 172 is open so that a guide wire may exit the tip. Medicine or radiographic fluid may also be injected distal of the catheter through the guide wire lumen.

In use, the catheter 102 is inserted into the body of a patient so that the balloon is within a blood vessel. Heat exchange fluid is circulated into the inflow port 136, travels down the inflow lumen 130 and into the inner lumen 114 at the wall 162 at the end of the inflow lumen. The heat exchange fluid travels to the distal end of the inner lumen and through the slits 168 between the inner lumen 114 and the outer lumens 108, 110 and 112.

The heat exchange fluid then travels back through the three outer lumens of the balloon to the proximal end of the balloon. The outer lumens are wound in a helical pattern around the inner lumen. At some point along the proximal portion of the shaft, each outer lumen is located over the portion of the shaft having a window (154, 152, 148) to the outflow lumen and the outer balloon lumens have a plurality of slits (158, 156, 150) that are aligned with the windows. The heat transfer fluid passes through the slits (158, 156, 150) through the windows (154, 152, 148) and into the outflow lumen 132. From there it is circulated out of the catheter through the outflow port 138.

Counter-current circulation between the blood and the heat exchange fluid is highly desirable for efficient heat exchange between the blood and the heat exchange fluid. Thus if the balloon is positioned in a vessel where the blood flow is in the direction from the proximal toward the distal end of the catheter, for example if it were placed from an insertion point in the femoral vein into the ascending vena cava, it is desirable to have the heat exchange fluid in the outer balloon lumens flowing in the direction from the distal end toward the proximal end of the catheter, as is the arrangement describe above. It is to be readily appreciated, however, that if the balloon were placed so that the blood was flowing along the catheter in the direction from distal to proximal, for example if the catheter was placed into the ascending vena cava from an insertion point in the jugular vein, it would be desirable to have the heat exchange fluid circulate in the outer balloon lumens from the proximal end to the distal end. This could be accomplished by merely reversing which port is used for inflow direction and which for outflow.

In use, a physician may employ the method of the invention to place a patient in a hypothermic state. By use of the Seldginer technique, the physician may insert a heat exchange catheter having a heat exchange balloon into the femoral vein of the patient. The catheter is advanced until the heat exchange balloon is located in the inferior vena cava. The physician then utilizes the heat exchange system to circulate cold saline through the heat exchange balloon, which removes heat from the blood flowing past the heat exchange balloon. The physician continues to utilize the heat exchange system for a sufficient length of time to reduce the temperature of the patient.

Simultaneously the physician administers an antithermoregulatory response mechanism in the manner and at the dosage/duration as described above. The physician may administer a bolus amount of agent or warmth and subsequent maintenance amounts of agent or warmth, or may administer the agent or warmth in any other effective manner. In any event, when the patient's temperature falls below the shivering threshold, the level of anti-thermoregulatory response agent in the patient or level of warmth applied to the patient will be sufficient to reduce shivering. This in turn makes the reduction in temperature by the heat exchange system more effective, and reduces the discomfort and other adverse effects of shivering.

When the patient has reached the target temperature below the shivering threshold, the level of antithermoregulatory response agent or application of warmth is maintained at an effective level, so that the heat exchange system can maintain the patient precisely at the target temperature. The system has one or more patient temperature monitors that provide feedback to the control unit for the system. Since the amount of metabolic heat generated by the body is reduced, and since the thermoregulatory response mechanisms of the body are not actively opposing the temperature control of the heat exchange system by shivering, the target temperature can more safely and more precisely maintain the patient at the target temperature.

When the physician wishes to re-warm a patient slowly from a hypothermic condition below the shivering threshold, he or she may employ the method of the invention to more precisely control the rate of warming. When the patient has an effective level of anti-thermoregulatory response agent or has an effective level of warmth applied so as to reduce shivering, the physician may activate the heat exchange system to begin in vivo core warming. The feedback from the patient temperature monitors allows control of the heat exchange system to slowly warm the patient, or to slightly cool the blood of the patient if the patient's own body is functioning to warm the patient too fast. Because the very effective shivering mechanism is reduced or eliminated, the heat exchange system has sufficient power and precision to maintain the gentle rate of warming and prevent the body from re-warming too fast.

In each of the above examples, the anti-thermoregulatory response mechanism can be administered before the heat exchange begins, or may be administered only upon the initiation of shivering, or any appropriate manner.

Application to Specific Medical Conditions

There are various medical conditions as described below where the application of hypothermia to a particular patient presents a significant advantage, or where it is important to carefully control a patient temperature at some temperature below the patient's shivering threshold. If the patient is paralyzed by general anesthesia and intubated with a breathing tube, shivering is generally not a problem when the patient is cooled below what would otherwise be the shivering threshold. However, if it is either necessary or desirable to cool or control the temperature of a patient not under general anesthesia, shivering should be controlled. Below are several examples were the application of temperature control below the shivering threshold, combined with the application of anti-thermoregulatory response mechanisms makes the generally use of therapeutic hypothermia and temperature control feasible for the first time.

1. Myocardial Infarct ("MI")

When a person experiences a blockage in one of the arteries that supplies blood to the heart muscle (usually by a blood clot), the result is a myocardial infarct, often called a heart attack. The area of the heart which is deprived of needed blood is at risk for permanent cell death. Medical treatment of the patient is designed to restore blood flow to the tissue as quickly as possible, and to protect the area of heart tissue at risk from permanent cell death.

Currently when a victim of a heart attack is admitted to a hospital, the standard of care involves one of three courses of action: (1) application of thrombolytics (clot busting drugs) in an attempt to dissolve the clot and restore blood flow to the affected tissue, i.e., establish reperfusion; (2) angioplasty of the affected artery, with or without a stent to hold the vessel open after angioplasty; and (3) conservative medical treatment, i.e., management of symptoms. Any of these courses of action may or may not be followed by coronary artery by-pass surgery. The ultimate goal, of course, is to maximize the amount of active, functional heart tissue that survives after the heart attack.

In all of the above treatment scenarios, the application of cooling to the heart tissue may have dramatic therapeutic value and can be easily achieved by the cooling devices described in this application. Furthermore, the control of the temperature as described may have significant advantages, particularly in the re-warming of the patient after hypothermia has been induced and maintained for some time.

Although the exact mechanisms by which hypothermia is tissue protective are not fully understood, it is believed that there are various reasons why the application of cooling to the heart tissue may be advantageous: the reduction of the metabolic rate with resultant preservation of energy stores when the tissue is deprived of blood may be helpful; the cooling may reduce membrane permeability to damaging ions and enzymes; certain harmful biochemical cascades may be interrupted or prevented; the damaging release of certain enzymes or other substances, particularly those associated with inflammation, may be prevented; the activation or aggregation of platelets may be prevented and thus prevent microvascular damage; and the cooling may result or assist in the induction of various substances to allow adaptation to ischemia such as heat shock proteins or mitochondrial biogenesis.

Whatever the mechanism, the cooling of the myocardium during or shortly after an MI to hypothermic levels, generally at least below 35° C. and even as low as 32° C., has been found to be very protective. If the heat exchange region of the catheter, for example the balloon in the heat exchange balloon catheter described above, is placed in the inferior vena cava ("IVC"), the cooled blood flows directly into the heart chamber and has been found to cool the entire heart very effectively. Because the cooling is not limited to areas of the heart muscle that are receiving arterial blood, even portions of the heart that are suffering a lack of normal perfusion will be cooled and protected. If the heart is cooled, the blockage that caused the heart attack is removed either by angioplasty or application of thrombolytics, the heart is maintained at a cool temperature for some time to prevent reperfusion injury such as microvascular injury due to platelet activation or aggregation, and then the heart is slowly and controllably re-warmed, damage to the heart cells may be limited.

In the treatment of a victim of a heart attack, the patient is almost always awake and not anesthetized and intubated. Critical symptoms such as pain are verbally communicated by the patient to the doctor, and the patient needs to respond to verbal commands from the doctor, and it is preferable that various physiological parameters be unaffected by anesthesia. Therefore even though the patient may be mildly sedated (consistent with the anti-thermoregulatory response agent regime applied in such a case) they are awake and responsive, even during angioplasty. To use hypothermia effectively in such a case, the control of shivering and/or vasoconstriction is important.

An exemplary hypothermia treatment of a patient that has suffered a myocardial infarct comprises the following steps:

(i) administering an initial bolus dose of a first anti-thermoregulatory response agent to the patient (for example an oral dose of a serotonin 5 HT1a receptor agonist such as 60 mg of buspirone);

(ii) administering a subsequent dose of a second anti-thermoregulatory response agent to the patient (for example an intravenous dose of an $\mu$ opioid receptor agonist such as 50 mg of meperidine administered by slow push and infused over about 5 minutes);

(iii) optionally applying warmth to the skin of the patient (a warming blanket); and (iv) an intravenous temperature control catheter of the general type described above is introduced and the heart exchange region of the catheter is placed in the IVC and cooling is begun at the maximum rate. The patient is thereafter maintained at a therapeutically low temperature for a sufficient time to treat the myocardial infarct.

Commercially available warming blankets for use in step (iii) include the Bair Hugger by Augustine Medical, which may be placed on high for maximum heat. The heating blanket should apply, for example, about a temperature of about 43° C. to the skin of the patient. In step (iv), the patient has the cooling catheter placed into the vascular system in the manner well known to medical practitioners who place catheters. The procedure may take place in the emergency room, or even in the ambulance on the way to the emergency room. Generally the earlier the hypothermia is begun, the better for salvage of myocardial tissue, but the anti-thermoregulatory response mechanism must be effective by the time the patient is cooled to the shivering threshold. Temperature sensors are placed on or in the patient and attached to the controller. It has been found that esophageal temperature probes provide a relatively accurate representation of the heart temperature and therefore are particularly useful in the protocol for the treatment of MI. A target temperature is set and the system cools toward the target temperature.

This treatment can also further comprise a step, where after administering the second anti-thermoregulatory response agent in step (ii), a second dose of the second anti-thermoregulatory response agent is administered. For example, step (ii) can involve administering an intravenous dose of 50 mg of meperidine, which would then be followed about 15 minutes by a second dose of about 50 mg of meperidine administered by slow IV push followed by a constant IV administration of about 25 mg/hr of meperidine. In addition, a supplemental bolus of 25 mg IV of meperidine or an increase in the rate of constant administration may be applied at the option of the physician as needed to control shivering. Indeed, if shivering occurs, the treating physician may elect to increase the temperature of the patient slowly until the patient is above the shivering threshold. This is still generally within the hypothermic range, and even if the individual patient is not as cold as originally desired, the hypothermic treatment is believed to be very helpful. It has also been found that once shivering has begun, control of shivering is difficult and may require slight re-warming of the patient until the shivering stops. Once the shivering is under control, the patient often may be re-cooled and the shivering will often remain under control.

Once cooled to the target temperature (often about 32° C.) the controller will act to cease additional temperature reduction and begin temperature maintenance, keeping the patient at the target temperature. At this temperature, the patient is treated according to the current standard of care. This may include the administration of thrombolytic drugs, the performance of angioplasty ("PTCA") with or without stenting, or both. The presence of hypothermia is generally protective of the heart tissue and will not decrease the effectiveness of the thrombolytic treatment since the commonly used thrombolytic drugs, such as tPA, are generally not rendered significantly less effective when administered to a hypothermic patient. Likewise, the presence of the temperature control catheter in the IVC of the patient does not interfere with the placement of the PTCA catheter through the arterial system, i.e. up the femoral artery and aorta and into the coronary arteries, so the application of hypothermia does not interfere with this standard treatment. In short, the application of hypothermia is adjunctive to current treatment and does not prevent or even significantly interfere with other treatment. Application of the IV drip of meperidine and the warming blanket should be continued at all times while the patient is cooler than the shivering threshold, even during angioplasty.

If the patient has undergone angioplasty, the time of reperfusion will generally be clearly known. However, if the patient is administered thrombolytic drugs, the exact time of reperfusion will often not be known, but may be roughly determined by the treating physician. In either event, the patient should generally be kept hypothermic (cooler than 35° C. and perhaps as cool as 32° C.) for about 4 hours after reperfusion. It is believed that various reperfusion injuries of the heart tissue, including various inflammation mechanisms are generally activated or occur during this 4 hour time period.

After the post reperfusion time period, a new target temperature is entered, generally normothermia, and patient is generally re-warmed to normothermia as quickly as feasible, perhaps 2 or 3° C. per hour. The patient should receive the anti-thermoregulatory response agent such as an IV dose of meperidine at the dosage described above, and the application of the warming blanket during this entire time until the patient has warmed above the shivering threshold.

The exact time duration of cooling therapy, drug doses and the like are suggested modes of practicing the invention but are not intended to limit the application of the method to the specific examples given.

2. Stroke

The disease categorized as stroke is extremely variable, and therefore the treatment will similarly be extremely variable. Similar to an MI, the stroke is often caused by a blockage in the blood supply to portions of the brain, sometimes caused by a clot in the vasculature that delivers blood to part of the brain (ischemic stroke) and sometimes caused by a breakage in the vasculature, interrupting blood supply and putting pressure on part of the brain (hemorrhagic stroke). In either case, for continued treatment and evaluation, it is important that the patient remain awake; alertness, the ability to respond to verbal commands and the ability of the physician to monitor various physiological parameters such as eye movement and muscle strength and tone are destroyed or impaired by general anesthesia. However, it is known that hypothermia is very neuroprotective, and the ability of brain tissue to survive the initial insult of deprivation of blood, particularly the ability of the larger area surrounding the focus of the insult, an area often called the penumbra, to survive and return to normal function is significantly enhanced if the brain can be cooled during or immediately after the stroke. Therefore a method of cooling an awake patient is critical to treating this disease with hypothermia. What is described here is merely one example of how a treating physician might use hypothermia in combination with anti-thermoregulatory response mechanism to treat a stroke victim.

Shivering must be suppressed while hypothermia is being maintained, for the comfort of the patient, (violent shivering would be so uncomfortable that it generally could not be tolerated), for the metabolic health of the patient (shivering would soon exhaust the patient, a highly undesirable situation for a patient who is generally very ill), and if the disease condition permits, so the patient can be awake and conscious for purposes of continued monitoring. Indeed, unless shivering is suppressed, it may not even be possible to induce hypothermia. The amount of metabolic heat generated by shivering may be so significant that even a cooling catheter capable of removing 200 or 300 watts of energy may not be able to break through the shivering threshold and effectively induce hypothermia.

Additionally in the case of stroke, it is important to re-warm the patient after a long period of hypothermia very slowly and under strict temperature control. Shivering must be suppressed during controlled re-warming, or even a very powerful temperature control catheter will not be able to prevent the patient's temperature from running away and fast re-warming and possible overshoot. For all those reasons, the treatment of stroke with hypothermia generally needs to be accompanied by an anti-thermoregulatory regime.

After a patient is initially diagnosed as suffering from a stroke, a recommended treatment may comprise the following steps:

(i) administering an initial bolus dose of a first anti-thermoregulatory response agent to the patient (for example an oral dose of a serotonin 5 HT1a receptor agonist such as 30 mg of buspirone);

(ii) administering a first dose of second anti-thermoregulatory response agent to the patient (for example an intravenous dose of an $\mu$ opioid receptor agonist such as 50 mg of meperidine administered by slow push and infused over about 5 minutes);

(iii) administering a second dose of the second anti-thermoregulatory response agent to the patient (for example, about 15 minutes after the initial administration of meperidine, an additional 50 mg of meperidine is administered by slow IV push);

(iv) administering a third dose of the second anti-thermoregulatory response agent by constant IV administration (for example, constant IV administration of about 25 mg/hr of meperidine maintained for the duration of the time that the patient's temperature is below the shivering threshold);

(v) an intravenous temperature control catheter of the general type described above is introduced into the vasculature of the patient and the heart exchange region of the catheter is placed in the IVC and cooling is begun at the maximum rate. The patient is thereafter maintained at a therapeutically low temperature for a sufficient time to treat the stroke.

Warmth can be also be applied to the skin of the patient (for example, by a warming blanket) at any time, but would typically occur after step (i). Once the target temperature is reached, the controller acts to maintain the patient at the target temperature for a long period of time, depending on the patient and the severity of the stroke, for example, for 24 hours, 36 hours, 72 hours, or perhaps even longer. After maintaining the target temperature for the desired length of time, the controller can be set to re-warm the patient to normothermia at a predetermined rate, for example 0.2° C. per hour.

This method of treatment includes an initial oral dose of a second anti-thermoregulatory response agent such as 30 mg of the serotonin 5 HT1a receptor agonist buspirone. For the remainder of the time the patient is cooled or maintained below the shivering threshold, the patient can continue to receive orally dosages of the second anti-thermoregulatory response agent such as a 30 mg or 60 mg dose of buspirone per dose. Generally, 90 mg buspirone per day is generally considered the maximum dose, and in the case of MI or elective PTCA, only one initial dose is used because the treatment period is generally less than 8 hours. Because only one dose is administered, the full 60 mg is administered. However, in stroke, long and continuous administration of the anti-thermoregulatory regime is involved, and therefore 30 mg every 8 hours is generally administered.

The controller is set so the patient is cooled in step (iv) to a pre-selected target temperature, for example 32° C. as quickly as possible, for example in approximately half an hour. Even if the cooling takes much longer, for example several hours, it is still advantageous to cool the patient to a hypothermic level. During temperature maintenance, it is important to maintain the anti-thermoregulatory regime. Accordingly, the temperature maintenance step can be accompanied by the administration of one or more anti-thermoregulatory response agents. For example oral doses of buspirone at the rate of 30 mg every 8 hours, and an IV drip of 25 mg/hr of meperidine will generally be maintained. Additional drugs can also be administered to maintain a suitable level of mild sedation that will allow monitoring and treatment of the patient's neurological condition but prevent shivering. Even though fever during stroke is generally associated with negative outcome, skin warming is generally applied throughout this period. For example, the patient may be wrapped in a warmning blanket with the blanket on a high setting. It is the patient's core temperature and thus the temperature of the patient's brain that is important, and that temperature is hypothermic even if the skin is warmed. If shivering does occur, additional measures should be taken to stop the shivering, for example, an application of additional anti-thermoregulatory drug doses, different drugs, the application of additional surface warming, or any combination of these measures may assist in eliminating the shivering. It may even be necessary as described above in the section concerning the treatment of MI, to temporarily increase the temperature of a shivering patient until the shivering is brought under control.

At the end of treatment, it is generally believed that it is important to warm very slowly from hypothermia back to normothermia. The method of controlling this re-warming rate has been previously described. If a patient is allowed to re-warm spontaneously, even without shivering, the rate is generally far faster than what is desirable, and may occur in dramatic spurts rather than a controlled manner. If the patient is allowed to shiver, the problem is even worse and the rate is much faster. Even if the patient has the warming catheter and control unit operational as described above, shivering is such a powerful thermoregulatory force that it generally makes control of the re-warming process difficult or impossible, overwhelming the ability of the cooling/warming catheter to gently control the rate of warming. Without shivering, however, the cooling/warming device subject to the control as described above, is able to control the re-warming rate very tightly, for example, to cause the patient to re-warm at, for example, 0.2° C. per hour for as long as necessary to reach normothermia. Because the uncontrolled body would normally warm faster than this, the temperature catheter system acts to remove excess heat from the body as it warms and keep the re-warming rate slow.

3. Elective PTCA

Elective percutaneous transluminal coronary angioplasty ("PTCA") is a common procedure for treatment of a blockage of coronary arteries where the patient is not suffering a heart attack but where there is a need to open clogged or critically narrowed coronary arteries. This is generally done by inserting a guide wire percutaneously into the vasculature of a patient, steering it up the aorta, through the ostium, into the coronary arteries and over the clogged or narrow portion of the artery. A balloon catheter is then steered over the guide wire until the balloon is located across the narrowing. The balloon is then inflated, presses against the sides of the clogged artery and hopefully dilates the narrowing. The inflation of the balloon may be repeated several times. Sometimes a stent is placed in the artery where the dilatation has occurred to help hold the vessel open. This is usually done by placing a compressed stent over a deflated balloon, steering the balloon to the proper location in the arteries much as with PTCA, and inflating the balloon to expand the stent in the vessel.

Whenever a balloon is fully inflated and presses into the wall of the vessel, for example during dilatation or stent expansion, the vessel is blocked and the myocardium downstream of the blockage is deprived of its normal blood flow. Even if the balloon is not inflated but is steered into a narrowed artery, it creates at least a partial blockage of the vessel and deprives the tissue downstream of some of the blood that might otherwise have reached that tissue. In addition, various particulate matter from the area of coronary stenosis, or platelet plugs may be released during balloon inflation, migrate distally, and occlude the microvasculature, resulting in ischemia to the downstream cells.

It would clearly be advantageous to provide tissue protection by cooling the heart tissues before, at the time of, and for some time after the blockages of the blood flow by balloon inflation and manipulation in general during elective PTCA. In most cases, however, elective PTCA is performed under mild sedation with the patient awake, and shivering would present an unacceptable obstacle to cooling. The discomfort, the exhaustion and the shaking would all unacceptable. Additionally, as mentioned above, the additional metabolic heat created by the shivering might well make it difficult or impossible to induce hypothermia, or to control body temperature if hypothermia was induced. Therefore control of shivering is necessary in order to induce hypothermia during elective PTCA.

The use of hypothermia and the protocol to combat shivering is very similar to that used in treatment of an MI which is also treated with PTCA. The difference, of course, is that the time urgency is far less in elective PTCA. A typical therapeutic regime would comprise the steps of:

(i) administering an initial bolus dose of a first anti-thermoregulatory response agent to the patient (for example an oral dose of a serotonin 5 HT1a receptor agonist such as 60 mg of buspirone);

(ii) administering a subsequent dose of a second anti-thermoregulatory response agent to the patient (for example an initial intravenous dose of an $\mu$ opioid receptor agonist such as 50 mg of meperidine administered by slow push followed by a similar second dose); and (iii) administering a further dose of the second anti-thermoregulatory response agent by constant IV administration (for example, constant IV administration of about 25 mg/hr of meperidine).

A warming blanket is wrapped around the patient as soon as possible, usually about the time the first anti-thermoregulatory response agent is administered. As soon as the physician believes that the anti-thermoregulatory response mechanism is operating, the cooling catheter is placed and cooling is begun. Because the urgency to begin the cardio- protective cooling is less with elective PTCA, the physician generally can be more cautious that the anti shivering mechanism is in effect before beginning the cooling than with the MI. The patient is thereafter maintained at a therapeutically low temperature for a sufficient time to perform the elective PTCA.

The patient is cooled as quickly as possible until the heart has reached a target temperature that is cardio protective, generally below 35° C. and usually about 32° C. Because of the volume of blood that must be cooled to cool the heart, this results in whole body cooling, so any temperature probe that senses the body temperature is likely to be sufficient to provide feedback to the controller for controlling this cooling. However, it has been found that one of the most accurate measures of cardiac temperature is esophageal temperature, so probes placed in the esophagus may be used to provide temperature feedback to the controller for temperature control.

Once the target temperature is reached, the controller acts to maintain the heart temperature at the target temperature while PTCA is performed. The heart is generally maintained at a hypothermic temperature for 3 or 4 hours after the PTCA is performed, and the then the controller is reset so that the patient is re-warmed to normothermia. Because the heart muscle is generally more robust than the brain tissue, the re-warming may generally be faster than is the case with stroke. Because the patient is generally not released from the Cardio-Intensive Care Unit until the patient is no longer hypothermic, re-warming is preferably fairly fast, possibly in one or two hours. As soon as the patient is warmed above the shivering threshold, the anti-thermoregulatory response mechanisms can be discontinued.

4. Maintaining Normothermia in Stroke and Head Trauma

Elevated temperature such as fever has been associated with very poor outcomes in victims of stroke or head trauma. It may also cause increased intra-cranial pressure ("ICP") which in turn may cause additional permanent neurological damage or even death. Therefore it is advantageous to apply the temperature control described in this application to a patient who has suffered traumatic brain injury or stroke for the purpose of maintaining normothermia and preventing fever. If the patient's body has a set point that is significantly above normothermia (37° C.) that patient may also have a shivering threshold that is above normothermia. In such a case, the mere application of cooling to bring a patient's temperature to normothermia may induce shivering. Shivering may generate sufficient metabolic heat to overpower the effects of a cooling catheter and make temperature reduction impossible, even just a reduction to normothermia. If the patient is suffering a stroke or brain injury, it may be important not to make them unconscious by general anesthesia and therefore a less severe anti-thermoregulatory regime as detailed above is applied.

The amount of shivering suppression is generally less in the case of fever prevention than in the case of stroke. As a result the amount of drug applied will often be less, with the exact amount determined by titrating to the need of the individual patient. Ironically, and counter-intuitively, it is also helpful to apply surface warming, such as a warming blanket, to a patient in order to reduce that patient's temperature. In fact, the application of surface warming may in fact be sufficient in itself to prevent shivering and no drugs may be needed.

The temperature control is applied by the controller in combination with the cooling system as described above, and may last as long as necessary to avoid the risk of injury by fever causing dangerously elevated ICP. For example, the stroke patient may be maintained at normothermia for several days, or even more than a week, and the patient with brain injury may be maintained at normothermia for a similar length of time.

5. Cardiogenic Shock

Approximately 7% of patients presenting with acute myocardial infarction also experience cardiogenic shock. Cardiogenic shock is the result of a vicious cycle, beginning with an anatomical or functional obstruction in the coronary bed. This obstruction leads to persistent ischemia, the end-result of which is myocardial infarction.

If the infarct is of sufficient size, it lowers both aortic pressure and coronary perfusion pressure (further hypotension), resulting in significant systemic ischemia. Thus, when a large enough section of the left ventricle becomes ischemic or necrotic, overall left ventricular function is depressed to the point at which circulation cannot be sustained and cardiogenic shock results. Mortality rates for MI complicated by cardiogenic shock are approximately 45.9–70%.

Before this invention, there were few viable treatment options for patients exhibiting symptoms of cardiogenic shock secondary to acute myocardial infarction. With the method of this invention, however, hypothermic treatment is possible. Even a patient suffering from cardiogenic shock generally has sufficient blood flow to achieve hypothermia when the heat exchange catheter is positioned with the heat exchange region in the IVC. The induction of hypothermia is protective in that it may: 1) slow cardiac metabolism to the point that myocardial ischemia is lessened or eliminated, preventing the domino-effect of adverse symptoms leading to a breakdown in heart function and circulation; and 2) reduce tissue metabolism throughout the body, allowing better preservation of organ function in the presence of reduced cardiac output.

The patients treated will generally not be paralyzed and intubated. Furthermore, it is often necessary to keep the patient awake for neurological examination and diagnosis. Therefore it will be necessary to control shivering while administering hypothermia. The patient who has suffered cardiogenic shock, besides the MI injury which requires treatment as described above, has generally suffered a period of systemic ischemia due to failure of circulation, and therefore should be treated with a prolonged period of hypothermia similar to that applied with stroke. For these reasons, the suggested anti-thermoregulatory protocol more closely resembles that of stroke rather than that used with MI.

After a patient is initially diagnosed as suffering from cardiogenic shock secondary to MI, a recommended treatment may comprise the following steps:

(i) administering an initial dose of a first anti-thermoregulatory response agent to the patient (for example an oral dose of a serotonin 5 HT1a receptor agonist such as 30 mg of buspirone);

(ii) optionally applying warmth to the skin of the patient (for example, by applying a warming blanket, preferably with the blanket on a high setting);

(iii) administering at least one dose of a second anti-thermoregulatory response agent to the patient (for example an initial intravenous dose of an $\mu$ opioid receptor agonist such as 50 mg of meperidine administered by slow push followed by a similar second dose); and (iv) administering a further dose of the second anti-thermoregulatory response agent by constant IV administration (for example, constant IV administration of about 25 mg/hr of meperidine); and (v) an intravenous temperature control catheter of the general type described above is introduced into the vasculature of the patient and the heart exchange region of the catheter is placed in the IVC and cooling is begun at the maximum rate. The patient is thereafter maintained at a therapeutically low temperature for a sufficient time to treat the cardiogenic shock.

Since the treatment is likely to continue for as long as several days, a continuous treatment with buspirone every 8 hours is likely, so the initial dose is preferably 30 mg rather than 60mg. As noted above, the initial dose of meperidine is generally 50 mg slow IV push and the second 50 mg slow push IV of meperidine is generally administered about 15 minutes after the first. Finally, a meperidine drip at about the rate of 25 mg /hr is established. The 30 mg oral dose of buspirone can be repeated at least once, and typically approximately every 8 hours. The 25 mg /hr meperidine drip is continued for the duration of the time that the patient is cooled to a temperature below the shivering threshold. (As is the case in all these drug dosages, the amount is believed to be an approximation of the correct dose, but the physician will generally titrate the amount based on the individual patient and the individual situation.)

In step (v), the temperature sensors are placed on or in the patient and connect to the controller, which is operated to control the system to achieve a target temperature, generally around 32° C., based on the signals received from the temperature sensors. While the patient is maintained at a therapeutically low temperature, one or more invasive measures can be initiated, followed by an assessment of the patient's condition. Invasive measures can be initiated in the intensive care unit, the emergency department, or in the catheterization laboratory and typically can include the insertion of an intra arterial balloon pump and/or the insertion of Swan Ganz catheter for measurements of central venous pressure and cardiac output. The physician will then assess the patient's condition and determine that the patient falls into one of three categories:

(i) the patient is stable and able to undergo PTCA;

(ii) the patient is stable but PTCA may be difficult and the patient is referred for a coronary artery by-pass graft procedure ("CABG") or intracoronary thrombolytic therapy; or (iii) the patient unstable and the physician will maintain current therapy until the patient is stable enough to proceed with PTCA or CABG.

For patients who ultimately undergo PTCA, the patient is immediately cooled as quickly as possible to a target temperature of about 32° C. After that target temperature is reached, the catheter system maintains hypothermia at about 32° C. during PTCA, and then for some time thereafter, which is typically a substantial period such as one day or even for as long as several days.

For patients referred for CABG surgery, the patient will be paralyzed and intubated during surgery, so no anti-thermoregulatory treatment is necessary during the procedure. Cooling will be initiated in the emergency room or in the catheterization laboratory, with a target temperature of about 32° C. The CABG is performed while the patient is at this temperature. If the patient is placed on a heart-lung by pass machine, the machine generally also includes a blood temperature that will control the patient's temperature, often keeping the patient in a hypothermic state during surgery.

After the initial treatment, it will generally be desirable to maintain a patient that has suffered cardiogenic shock in a hypothermic state for sometime, a day or even a week, and to re-warm the patient very slowly and in a very controlled manner. During that time the patient is generally mildly sedated to avoid shivering, but in an awake state. The general drug regime that may accomplish this is a meperidine drip of about 25 mg/hr and oral doses of buspirone of about 30 mg every 8 hours.

When the patient has been maintained for the desired period in a hypothermic state, the patient is re-warmed in a very slow (0.2° C./hr) and tightly controlled manner until he or she reaches normothermia.

6. Cardiac Arrest

Application of hypothermia after cardiac arrest is very similar to stroke. The injury is systemic to neural tissue deprived of blood, not due to a blockage of the coronary vasculature as in stroke, but rather due to the arrest of the heart. The systemic hypothermia would be accompanied with anti-thermoregulatory response mechanisms, as is the case in stroke. The same drug and warming blanket regime would apply as it does in stroke. As in stroke, the hypothermia may be maintained for several days or longer, and re-warming should be very slow and very controlled.

7. Temperature Control over Awake Patient in General

Although specific details of the temperature catheter are described above, the method of this invention could clearly be practiced with various different intravenous temperature control catheters and systems. Also, although specific medical conditions are detailed above, the invention herein is not limited to the specific conditions discussed and has general applications to temperature control for patients in the awakened state. For example, the ischemia of one or more metabolically active organs such as the kidneys would benefit from hypothermia. In the case of a prolonged hypothermic period where general anesthesia with the requirement that the patient be treated in the ICU would be extremely expensive and the prolonged period of paralysis and intubation very harmful to the overall health of the patient hypothermia with anti-thermoregulatory response mechanisms that include only mild sedation and warming blankets is called for.

With the above examples as guides, those of skill in the art of treating various medical conditions where it is desirable to maintain temperature control over an awake patient for therapeutic purposes can readily adopt the techniques for their purposes, and the invention herein is limited only by the scope of the claims allowed.

Each of the patents, publications, and other published documents mentioned or referred to in this specification is herein incorporated by reference in its entirety.

While the present invention has been described with reference to the specific embodiments thereof, it should be understood by those skilled in the art that various changes may be made and equivalents may be substituted without departing from the scope of the invention. In addition, many modifications may be made to adapt a particular situation, material, composition of matter, process, process step or steps, while remaining within the scope of the present invention. Accordingly, the scope of the invention should therefore be determined with reference to the appended claims, along with the full range of equivalents to which those claims are entitled.

What is claimed is:

1. A method for controlling the temperature of all or a portion of a patient's body to a temperature below its set point temperature, while achieving thermoregulatory inhibition, comprising the steps of: (a) sensing the temperature of all or a portion of the patient's body; (b) generating a signal based upon the sensed temperature; (c) controlling the temperature of all or a portion of the patient's body based upon the signal by placing a heat exchange device having a heat exchange region into heat exchange proximity with the patient's body and controlling the temperature of the heat exchange region for a sufficient time to affect the temperature of all or a portion of the patient's body; and (d) administering a therapeutically effective amount of an anti-thermoregulatory response agent to the patient.

2. The method of claim 1 wherein thermoregulatory inhibition is the inactivation of the shivering response.

3. The method of claim 1 wherein thermoregulatory inhibition is the inhibition of vasoconstriction.

4. The method of claim 1 which further comprises applying warmth to the skin of the patient.

5. The method of claim 1 wherein the temperature controlling step (c) comprises lowering the temperature below the set point temperature.

6. The method of claim 1 wherein the temperature controlling step (c) comprises raising the temperature from an initial temperature below the set point temperature.

7. The method of claim 6 wherein the temperature controlling step (c) comprises raising the temperature at a predetermined rate.

8. The method of claim 6 wherein the temperature controlling step (c) comprises maintaining the temperature at a stable temperature below the set point temperature.

9. The method of claim 8 wherein the stable temperature is normothermia.

10. The method of claim 1 wherein the temperature controlling step (c) comprises placing a heat exchange device having a heat exchange region into the vascular system of the patient and controlling the temperature of the heat exchange region for a sufficient time to affect the temperature of all or a portion of the patient's body.

11. The method of claim 10 wherein the heat exchange device is a catheter and the heat exchange region comprises a balloon on the catheter, the temperature of the balloon being controlled by the circulation of a heat exchange fluid through the interior of the balloon.

12. The method of claim 11 wherein the balloon is multi-lobed.

13. The method of claim 11 wherein the temperature controlling step (c) comprises controlling the temperature of the heat exchange fluid.

14. The method of claim 11 wherein the temperature controlling step (c) comprises controlling the rate of circulation of the heat exchange fluid.

15. The method of claim 1 wherein the anti-thermoregulatory response agent is selected from the group consisting of: dopamine receptor blockers; dopamine receptor agonists; κ opioid receptor agonists; μ opioid receptor agonists; opioid agonist-antagonist analgesics; serotonin 5HT1a receptor agonists; α2-adrenoreceptor agonists; non-opiod analgesic monoamine uptake inhibitors; neuropeptides; and combinations thereof.

16. The method of claim 15 wherein the anti-thermoregulatory response agent is selected from the group consisting of chlorpromazine; thorazine; haloperidol; trans-3,4-dichloro-N-methyl-N-[2-(1-pyrrolidinyl)cyclohexyl] benzene acetamide; (5a,7a,8B)-N-methyl-N-[7-(1-pyrrolidinyl)-1-oxaspiro(4,5)-dec-8-yl]benzene acetamide; meperidine; pentazocine; butorphanol; nalbuphine; buspirone; dexmedetomidine; nepofam; neurotensin; and pharmaceutically acceptable salts and variants thereof.

17. The method of claim 16 wherein the anti-thermoregulatory response agent is a combination of meperidine and dexmedetomidine.

18. The method of claim 16 wherein the anti-thermoregulatory response agent is a combination of meperidine and buspirone.

19. A method for providing therapeutic temperature control of all or a portion of a patient's body to a temperature below its set point temperature while reducing shivering in a patient that is being treated for a medical condition, comprising the steps of: (a) sensing the temperature of all or a portion of the patient's body; (b) generating a signal based upon the sensed temperature; (c) controlling the temperature of all or a portion of the patient's body based upon the signal by placing a heat exchange device having a heat exchange region into heat exchange proximity with the patient's body and controlling the temperature of the heat exchange region to control the temperature of all or a portion of the patient's body; (d) administering an anti-thermoregulatory response mechanism to the patient; and (e) maintaining the temperature of all or a portion of the patient's body at a therapeutically low temperature for a sufficient time to treat the medical condition.

20. The method of claim 19 wherein the heat exchange device is a catheter and the heat exchange region comprises a balloon on the catheter, the temperature of the balloon being controlled by the circulation of a heat exchange fluid through the interior of the balloon.

21. The method of claim 20 wherein the balloon is multi-lobed.

22. The method of claim 20 wherein the temperature controlling step (c) comprises controlling the temperature of the heat exchange fluid.

23. The method of claim 20 wherein the temperature controlling step (c) comprises controlling the rate of circulation of the heat exchange fluid.

24. The method of claim 19 wherein the administering an anti-thermoregulatory response mechanism comprises administering a therapeutically effective amount of an anti-thermoregulatory response agent to the patient.

25. The method of claim 19 wherein the administering an anti-thermoregulatory response mechanism comprises applying warmth to the skin of the patient.

26. The method of claim 19 wherein the administering an anti-thermoregulatory response mechanism comprises administering a therapeutically effective amount of an anti-thermoregulatory response agent to the patient and applying warmth to the skin of the patient.

27. The method of claim 19 wherein the temperature controlling step (c) comprises lowering the temperature at a predetermined rate.

28. The method of claim 19 wherein the temperature controlling step (c) comprises maintaining the temperature at a stable temperature below the set point temperature.

29. The method of claim 19 wherein the patient has suffered a myocardial infarct.

30. The method of claim 29 wherein the therapeutic temperature control comprises cooling the heart tissue.

31. The method of claim 30 wherein the heat tissue is cooled to a temperature at least below 35° C.

32. The method of claim 29 wherein the temperature controlling step (c) comprises placing a heat exchange device having a heat exchange region into the inferior vena cava of the patient.

33. The method of claim 29 wherein administration of the anti-thermoregulatory response mechanism step (d) occurs prior to initiation of the temperature controlling step (c).

34. The method of claim 19 wherein the patient has suffered a myocardial infarct and the administration of the anti-thermoregulatory response mechanism step (d) occurs prior to initiation of the temperature controlling step (c), and wherein step (d) comprises the steps of: (i) administering an initial bolus dose of a first anti-thermoregulatory response agent to the patient; and (ii) administering a subsequent dose of a second anti-thermoregulatory response agent to the patient.

35. The method of claim 34 wherein step (d) further comprises applying warmth to the skin of the patient.

36. The method of claim 34 wherein step (c) comprises placing a heat exchange device having a heat exchange region into the inferior vena cava of the patient.

37. The method of claim 34 wherein the first anti-thermoregulatory response agent is a serotonin 5 HT1a receptor agonist and the second anti-thermoregulatory response agent second is a κ opioid/μ opioid receptor agonist.

38. The method of claim 37 wherein the serotonin 5 HT1a receptor agonist is buspirone and the κ opioid/μ opioid receptor agonist is meperidine.

39. The method of claim 34 which further comprises administering a subsequent dose of the second anti-thermoregulatory response agent by constant IV administration.

40. The method of claim 19 wherein the patient has suffered a stroke.

41. The method of claim 40 wherein the temperature controlling step (c) comprises placing a heat exchange device having a heat exchange region into the inferior vena cava of the patient.

42. The method of claim 40 wherein the temperature maintenance step (e) is followed by a step comprising re-warming the patient to normothermia at a predetermined rate.

43. The method of claim 40 wherein administration of the anti-thermoregulatory response mechanism step (d) occurs prior to initiation of the temperature controlling step (c).

44. The method of claim 19 wherein the patient has suffered a stroke and the administration of the anti-thermoregulatory response mechanism step (d) occurs prior to initiation of the temperature controlling step (c), and wherein step (d) comprises the steps of: (i) administering an initial bolus dose of a first anti-thermoregulatory response agent to the patient; (ii) administering a first dose of a second anti-thermoregulatory response agent to the patient; (iii) administering a second dose of the second anti-thermoregulatory response agent to the patient; and (iv) administering a third dose of the second anti-thermoregulatory response agent by constant IV administration.

45. The method of claim 44 wherein step (d) further comprises applying warmth to the skin of the patient.

46. The method of claim 44 wherein step (c) comprises placing a heat exchange device having a heat exchange region into the inferior vena cava of the patient.

47. The method of claim 44 wherein the first anti-thermoregulatory response agent is a serotonin 5 HT1a receptor agonist and the second anti-thermoregulatory response agent is a κ opioid/μ opioid receptor agonist.

48. The method of claim 47 wherein the serotonin 5 HT1a receptor agonist is buspirone and the κ opioid/μ opioid receptor agonist is meperidine.

49. The method of claim 44 wherein the temperature maintenance step (e) is accompanied by administration of one or more anti-thermoregulatory response agents.

50. The method of claim 19 wherein the patient has undergone elective percutaneous transluminal coronary angioplasty.

51. The method of claim 50 wherein the therapeutic temperature control comprises cooling the heart tissue.

52. The method of claim 50 wherein the temperature controlling step (c) comprises placing a heat exchange device having a heat exchange region into the inferior vena cava of the patient.

53. The method of claim 50 wherein administration of the anti-thermoregulatory response mechanism step (d) occurs prior to initiation of the temperature controlling step (c).

54. The method of claim 19 wherein the patient has undergone elective percutaneous transluminal coronary angioplasty and the administration of the anti-thermoregulatory response mechanism step (d) occurs prior to initiation of the temperature controlling step (c), and wherein step (d) comprises the steps of: (i) administering an initial bolus dose of a first anti-thermoregulatory response agent to the patient; and (ii) administering a subsequent dose of a second anti-thermoregulatory response agent to the patient.

55. The method of claim 54 wherein step (d) further comprises applying warmth to the skin of the patient.

56. The method of claim 54 wherein step (c) comprises placing a heat exchange device having a heat exchange region into the inferior vena cava of the patient.

57. The method of claim 54 wherein the first anti-thermoregulatory response agent is a serotonin 5 HT1a receptor agonist and the second anti-thermoregulatory response agent second is a κ opioid/μ opioid receptor agonist.

58. The method of claim 57 wherein the serotonin 5 HT1a receptor agonist is buspirone and the κ opioid/μ opioid receptor agonist is meperidine.

59. The method of claim 54 which further comprises administering a second dose of the second anti-thermoregulatory response agent by constant IV administration.

60. The method of claim 19 wherein the patient has suffered a head trauma.

61. The method of claim 60 wherein the administering an anti-thermoregulatory response mechanism comprises administering a therapeutically effective amount of one or more anti-thermoregulatory response agents to the patient.

62. The method of claim 60 wherein the administering an anti-thermoregulatory response mechanism comprises applying warmth to the skin of the patient.

63. The method of claim 60 wherein the administering an anti-thermoregulatory response mechanism comprises administering a therapeutically effective amount of one ore more anti-thermoregulatory response agents to the patient and applying warmth to the skin of the patient.

64. The method of claim 19 wherein the patient has suffered a head trauma and the administration of the anti-thermoregulatory response mechanism step (d) occurs prior to initiation of the temperature controlling step (c), and wherein step (d) comprises the steps of: (i) administering a first dose of an anti-thermoregulatory response agent to the patient; (ii) administering a second dose of the anti-thermoregulatory response agent to the patient; and (iii) administering a third dose of the anti-thermoregulatory response agent by constant IV administration.

65. The method of claim 64 wherein the anti-thermoregulatory response agent is a κ opioid/μ opioid receptor agonist.

66. The method of claim 65 wherein the κ opioid/μ opioid receptor agonist is meperidine.

67. The method of claim 19 wherein the patient has suffered cardiogenic shock.

68. The method of claim 67 wherein step (c) comprises placing a heat exchange device having a heat exchange region into the inferior vena cava of the patient.

69. The method of claim 67 wherein administration of the anti-thermoregulatory response mechanism step (d) occurs prior to initiation of the temperature controlling step (c).

70. The method of claim 19 wherein the patient has suffered cardiogenic shock and the administration of the anti-thermoregulatory response mechanism step (d) occurs prior to initiation of the temperature controlling step (c), and wherein step (d) comprises the steps of: (i) administering an initial dose of a first anti-thermoregulatory response agent to the patient; (ii) administering a second anti-thermoregulatory response agent to the patient; and (iii) administering a further dose of the second anti-thermoregulatory response agent by constant IV administration.

71. The method of claim 70 wherein step (d) further comprises applying warmth to the skin of the patient.

72. The method of claim 70 wherein step (i) is repeated at least once.

73. The method of claim 70 wherein step (c) comprises placing a heat exchange device having a heat exchange region into the inferior vena cava of the patient.

74. The method of claim 70 wherein the first anti-thermoregulatory response agent is a serotonin 5 HT1a receptor agonist.

75. The method of claim 74 wherein the serotonin 5 HT1a receptor agonist is buspirone.

76. The method of claim 74 wherein the second anti-thermoregulatory response agent is a κ opioid/μ opioid receptor agonist.

77. The method of claim 76 wherein the κ opioid/μ opioid receptor agonist is meperidine.

78. The method of claim 70 wherein the temperature maintenance step (e) is accompanied by one or more invasive measures, followed by an assessment of the patient's condition.

79. The method of claim 78 wherein the patient is assessed as being in a stable condition, the patient is immediately cooled to a target temperature of about 32° C., a percutaneous transluminal coronary angioplasty procedure is commenced, and the patient is maintained at that temperature for the duration of the procedure and for a specified time thereafter.

80. The method of claim 78 wherein the patient is assessed as being in a stable condition, the patient is cooled to a target temperature of about 32° C., a coronary artery by-pass graft procedure or intracoronary thrombolytic therapy is commenced, and the patient is maintained at that temperature for the duration of the procedure.

81. The method of claim 78 wherein the patient is assessed as being in an unstable condition, the patient is allowed to stabilize, the patient is then cooled to a target temperature of about 32° C., a coronary artery by-pass graft procedure or intracoronary thrombolytic therapy is commenced, and the patient is maintained at that temperature for some time thereafter.

82. The method of claim 19 wherein the patient has suffered cardiac arrest.

83. The method of claim 82 wherein the temperature controlling step (c) comprises placing a heat exchange device having a heat exchange region into the inferior vena cava of the patient.

84. The method of claim 82 wherein the temperature maintenance step (e) is followed by a step comprising re-warm the patient to normothermia at a predetermined rate.

85. The method of claim 82 wherein administration of the anti-thermoregulatory response mechanism step (d) occurs prior to initiation of the temperature controlling step (c).

86. The method of claim 19 wherein the patient has suffered cardiac arrest and the administration of the anti-thermoregulatory response mechanism step (d) occurs prior to initiation of the temperature controlling step (c), and wherein step (d) comprises the steps of: (i) administering a first dose of an anti-thermoregulatory response agent to the patient; (ii) administering a second dose of the anti-thermoregulatory response agent to the patient; and (iii) administering a third dose of the anti-thermoregulatory response agent by constant IV administration.

87. The method of claim 86 wherein step (d) further comprises applying warmth to the skin of the patient.

88. The method of claim 86 wherein step (c) comprises placing a heat exchange device having a heat exchange region into the inferior vena cava of the patient.

89. The method of claim 86 wherein the anti-thermoregulatory response agent is a κ opioid/μ opioid receptor agonist.

90. The method of claim 89 wherein the κ opioid/μ opioid receptor agonist is meperidine.

91. The method of claim 86 wherein step (d) is preceded by administering an initial oral dose of a second anti-thermoregulatory response agent.

92. The method of claim 91 wherein the second anti-thermoregulatory response agent is serotonin 5 HT1a receptor agonist and the anti-thermoregulatory response agent administered in step (d) is a κ opioid/μ opioid receptor agonist.

93. The method of claim 92 wherein the serotonin 5 HT1a receptor agonist is buspirone and the κ opioid/μ opioid receptor agonist is meperidine.

94. The method of claim 86 wherein the temperature maintenance step (e) is accompanied by administration of one or more anti-thermoregulatory response agents.

95. The method of claim 88 wherein the therapeutic temperature control comprises cooling the heart tissue.

96. The method of claim 19 wherein the patient is suffering from ischemia of one or more metabolically active organs.

97. The method of claim 96 wherein the anti-thermoregulatory response agent is selected from the group consisting of: dopamine receptor blockers; dopamine receptor agonists; κ opioid receptor agonists; μ opioid receptor agonists; opioid agonist-antagonist analgesics; serotonin 5HT1a receptor agonists; α2-adrenoreceptor agonists; non-opiod analgesic monoamine uptake inhibitors; neuropeptides; and combinations thereof.

98. The method of claim 97 wherein the anti-thermoregulatory response agent is selected from the group consisting of chlorpromazine; thorazine; haloperidol; trans-3,4-dichloro-N-methyl-N-[2-(1-pyrrolidinyl)cyclohexyl] benzene acetamide; (5a,7a,8B)-N-methyl-N-[7-(1-pyrrolidinyl)-1-oxaspiro(4,5)-dec-8-yl]benzene acetamide; meperidine; pentazocine; butorphanol; nalbuphine; buspirone; dexmedetomidine; nepofam; neurotensin; and pharmaceutically acceptable salts and variants thereof.

99. A method for raising the temperature of all or a portion of a patient's body from an initial temperature below the set point temperature, while reducing shivering, comprising the steps of: (a) sensing the temperature of all or a portion of the patient's body; (b) generating a signal based upon the sensed temperature; (c) raising the temperature of all or a portion of the patient's body based upon the signal by placing a heat exchange device having a heat exchange region into heat exchange proximity with the patient's body and controlling the temperature of the heat exchange region for a sufficient time to raise the temperature of all or a portion of the patient's body; and (d) administering an anti-thermoregulatory response mechanism to the patient.

100. The method of claim 99 wherein the administering an anti-thermoregulatory response mechanism comprises administering a therapeutically effective amount of an anti-thermoregulatory response agent to the patient or applying warmth to the skin of the patient or a combination thereof.

101. The method of claim 99 wherein the temperature controlling step (c) includes raising the temperature at a predetermined rate.

102. The method of claim 99 wherein the patient has undergone an operation.

103. The method of claim 99 wherein the temperature raising step (c) includes placing a heat exchange device having a heat exchange region into the vascular system of the patient and controlling the temperature of the heat exchange region for a sufficient time to affect the temperature of all or a portion of the patient's body.

104. The method of claim 99 wherein the anti-thermoregulatory response agent is selected from the group consisting of: dopamine receptor blockers; dopamine receptor agonists; κ opioid receptor agonists; μ opioid receptor agonists; opioid agonist-antagonist analgesics; serotonin 5HT1a receptor agonists; α2-adrenoreceptor agonists; non-opiod analgesic monoamine uptake inhibitors; neuropeptides; and combinations thereof.

105. The method of claim 104 wherein the anti-thermoregulatory response agent is selected from the group consisting of chlorpromazine; thorazine; haloperidol; trans-3,4-dichloro-N-methyl-N-[2-(1-pyrrolidinyl)cyclohexyl] benzene acetamide; (5a,7a,8B)-N-methyl-N-[7-(1-pyrrolidinyl)-1-oxaspiro(4,5)-dec-8-yl]benzene acetamide; meperidine; pentazocine; butorphanol; nalbuphine; buspirone; dexmedetomidine; nepofam; neurotensin; and pharmaceutically acceptable salts and variants thereof.

* * * * *